(12) United States Patent
Etzkorn

(10) Patent No.: US 10,004,433 B2
(45) Date of Patent: Jun. 26, 2018

(54) ELECTROCHEMICAL SENSOR CHIP

(71) Applicant: Verily Life Sciences LLC, Mountain View, CA (US)

(72) Inventor: James Etzkorn, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 597 days.

(21) Appl. No.: 14/325,219

(22) Filed: Jul. 7, 2014

(65) Prior Publication Data
US 2016/0003760 A1    Jan. 7, 2016

(51) Int. Cl.
*A61B 5/145*    (2006.01)

(52) U.S. Cl.
CPC ................. *A61B 5/14507* (2013.01)

(58) Field of Classification Search
CPC .... G01N 27/30; A61B 5/145; A61B 5/14507; A61B 5/14532; A61B 5/14546; A61B 5/1486; A61B 5/6821
See application file for complete search history.

(56) References Cited

U.S. PATENT DOCUMENTS

| | | | |
|---|---|---|---|
| 6,259,937 B1 * | 7/2001 | Schulman | A61B 5/14532 600/300 |
| 8,364,232 B2 | 1/2013 | Felder | |
| 8,627,712 B2 | 1/2014 | Donsky et al. | |
| 2005/0051440 A1 | 3/2005 | Simpson et al. | |
| 2005/0123680 A1 * | 6/2005 | Kang | A61B 5/14865 427/248.1 |
| 2008/0154101 A1 * | 6/2008 | Jain | A61B 5/0017 600/309 |
| 2008/0217173 A1 * | 9/2008 | Varney | G01N 27/4074 204/424 |
| 2010/0113901 A1 | 5/2010 | Zhang et al. | |
| 2011/0028807 A1 | 2/2011 | Abreu | |
| 2011/0311711 A1 | 12/2011 | Say et al. | |
| 2012/0201755 A1 | 8/2012 | Rozakis et al. | |
| 2012/0245444 A1 | 9/2012 | Otis et al. | |
| 2013/0150689 A1 | 6/2013 | Shaw-Klein | |

(Continued)

OTHER PUBLICATIONS

International Search Report and Written Opinion of International Application No. PCT/US2015/038776 dated Oct. 6, 2015.

*Primary Examiner* — Jacqueline Cheng
*Assistant Examiner* — Eric Messersmith
(74) *Attorney, Agent, or Firm* — McDonnell Boehnen Hulbert & Berghoff LLP

(57) ABSTRACT

An electrochemical sensor is disposed on a sensor substrate suitable for flip-chip mounting to another substrate. The electrochemical sensor can be fabricated in bulk by patterning sets of electrodes on a common substrate with vias that electrically couple each electrode to a conductive pad on the opposite side of the substrate. The substrate with electrodes thereon can then be diced and the individual electrochemical sensors can be flip-chip mounted in a body-mountable device in which the sensor can be used to obtain analyte concentrations. As a result, fabrication of the electrochemical sensor electrodes can be isolated from fabrication of the other electronics in the device, which can facilitate efficient fabrication of the sensor and allows for other electronics to be fabricated without restrictions associated with the electrode fabrication.

12 Claims, 12 Drawing Sheets

(56) References Cited

U.S. PATENT DOCUMENTS

2013/0225944 A1*  8/2013  Greco .................. A61B 5/04
                                            600/301
2014/0107444 A1    4/2014  Liu
2014/0107445 A1*  4/2014  Liu .................. A61B 5/0004
                                            600/345

* cited by examiner

ELECTROCHEMICAL SENSOR CHIP

BACKGROUND

Unless otherwise indicated herein, the materials described in this section are not prior art to the claims in this application and are not admitted to be prior art by inclusion in this section.

Electrochemical amperometric sensors measure concentrations of an analyte by measuring currents caused by oxidation or reduction reactions of the analyte in the presence of a charged electrode. Generally, a negatively charged electrode donates electrons to the analyte in a reduction reaction where the analyte becomes more negatively charged, whereas a positively charged electrode receives electrons from the analyte in an oxidation (or ionization) reaction where the analyte becomes more positively charged. The charged electrode (or working electrode) induces the reactions and receives or donates electrons to generate a current that provides the output signal. Thus, when the working electrode is appropriately charged, the output current is proportional to the reaction rate, which provides a measure of the concentration of the analyte surrounding the working electrode.

In some examples, an enzyme is fixed proximate the working electrode to selectively react with a desired analyte. For example, glucose oxidase can be fixed near the working electrode to react with glucose and release hydrogen peroxide, which is then electrochemically detected by the working electrode to indicate the presence of glucose. Other enzymes and/or reagents can be used to detect other analytes.

The eye is coated by a layer of tear film secreted by the lacrimal gland and distributed over the eye by motion of the eyelids. The tear film layer serves a number of biological functions including to lubricate and protect the corneal surface (epithelium). The tear film also includes several analytes that are present in blood, at concentrations that are related to their corresponding blood-analyte levels. Measuring the concentration of tear film analytes can therefore be used to diagnose and/or monitor various biological conditions.

SUMMARY

An electrochemical sensor is disposed on a sensor substrate suitable for flip-chip mounting to another substrate. The electrochemical sensor can be fabricated in bulk by patterning sets of electrodes on a single substrate with vias that electrically couple each electrode to a conductive pad on the reverse side of the substrate. The substrate with electrodes thereon can then be diced and the individual electrochemical sensors can be flip-chip mounted in a body-mountable device in which the sensor can be used to obtain analyte concentrations. As a result, fabrication of the electrochemical sensor electrodes can be isolated from fabrication of the other electronics in the device, which facilitates efficient fabrication of the sensor and allows for other electronics to be fabricated without restrictions associated with the electrode fabrication.

Some embodiments of the present disclosure can include a device. The device can include a polymeric material, a first substrate, an antenna, an electrochemical sensor, and a controller. The polymeric material can be formed to include a body-mountable surface. The antenna can be disposed on the first substrate. The electrochemical sensor can include a sensor substrate, a working electrode, a reference electrode, a first conductive connection pad, and a second conductive connection pad. The sensor substrate can be different from the first substrate. The sensor substrate can include a first side and a second side opposite the first side. The working electrode can be disposed on the first side of the sensor substrate. The reference electrode can be disposed on the first side of the sensor substrate. The first conductive connection pad can be disposed on the second side of the sensor substrate. The first conductive connection pad can be electrically coupled to the working electrode. The second conductive connection pad can be disposed on the second side of the sensor substrate. The second conductive connection pad can be electrically coupled to the reference electrode. The controller can be electrically connected to the electrochemical sensor via the first and second conductive connection pads. The controller can be disposed on the first substrate. The controller can be configured to: (i) apply a voltage between the working electrode and the reference electrode sufficient to generate an amperometric current related to the concentration of an analyte in a fluid to which the device is exposed; (ii) measure the amperometric current; and (iii) use the antenna to indicate the measured amperometric current.

Some embodiments of the present disclosure can include a method. The method can include forming, in a sensor substrate with a first side and a second side opposite the first side, a first depression and a second depression that extend into the first side, and terminate at respective distal ends within the sensor substrate. The method can include filling the first and second depressions with a conductive material that at least partially occupies the first and second depressions between the distal ends thereof and the first side of the sensor substrate. The method can include patterning, on the first side of the sensor substrate, a reference electrode. The method can include patterning, on the first side of the sensor substrate, a working electrode. The method can include polishing the second side of the sensor substrate so as to expose the first depression and the second depression, and the conductive material occupied therein.

Some embodiments of the present disclosure can include a method. The method can include applying, via a controller, a voltage between a working electrode and a reference electrode of an electrochemical sensor. The applied voltage can be sufficient to generate an amperometric current related to the concentration of an analyte in a fluid to which the electrochemical sensor is exposed. The working electrode and the reference electrode can each be disposed on a first side of a sensor substrate. A first conductive pad and a second conductive pad can be situated on a second side of the sensor substrate opposite the first side. The first conductive pad and the second conductive pad can be electrically coupled to the working electrode and the reference electrode, respectively. The controller can be disposed on a first substrate different from the sensor substrate. The controller can be electrically coupled to the working electrode and the reference electrode via the first conductive pad and the second conductive pad, respectively. The first substrate can be at least partially embedded in a body-mountable device. The method can include measuring the amperometric current using the controller. The method can include using an antenna disposed on the first substrate of the body-mountable device to indicate the measured current.

Some embodiments of the present disclosure include means for forming, in a sensor substrate with a first side and a second side opposite the first side, a first depression and a second depression that each extend into the first side, and each terminate at a distal end within the sensor substrate. Some embodiments of the present disclosure include means for filling the first and second depressions with a conductive material that at least partially occupies the first and second depressions between the first side and the distal ends thereof. Some embodiments of the present disclosure include means for patterning, on the first side of the sensor substrate, a reference electrode. Some embodiments of the present disclosure include means for patterning, on the first side of the sensor substrate, a working electrode. Some embodiments of the present disclosure include means for polishing the second side of the sensor substrate so as to expose the first and second depressions, and the conductive material occupied therein.

These as well as other aspects, advantages, and alternatives, will become apparent to those of ordinary skill in the art by reading the following detailed description, with reference where appropriate to the accompanying drawings.

DETAILED DESCRIPTION

Figure 1:
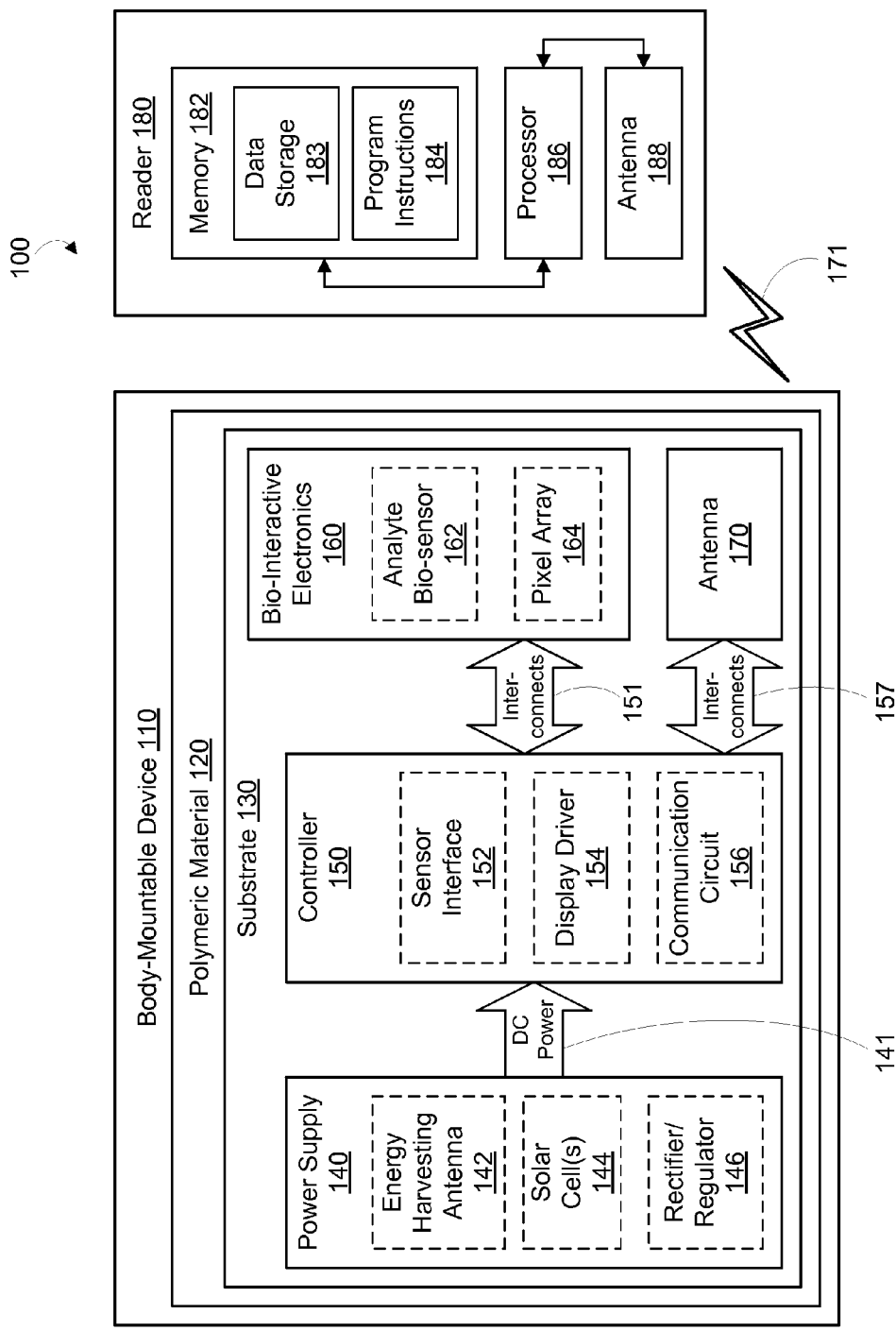
FIG. 1 is a block diagram of an example system that includes a body-mountable device in wireless communication with an external reader.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

An electrochemical sensor is disposed on a sensor substrate suitable for flip-chip mounting to another substrate. The electrochemical sensor can be fabricated in bulk by patterning sets of electrodes on a common substrate with vias that electrically couple each electrode to a respective conductive pad on the opposite side of the substrate. The substrate with electrodes thereon can then be diced and the individual electrochemical sensors can be flip-chip mounted in a body-mountable device in which the sensor can be used to obtain analyte concentrations. As a result, fabrication of the electrochemical sensor electrodes can be isolated from fabrication of the other electronics in the device, which can facilitate efficient fabrication of the sensor and allows for other electronics to be fabricated without restrictions associated with the electrode fabrication.

In some examples, the disclosed electrochemical sensor may be included in an eye-mountable device similar to a contact lens and the sensor may be used to measure properties of tear fluid that coats the contact lens. The contact lens can be formed of a polymeric material with embedded electronics configured to operate the sensor to obtain a measurement of analyte concentration and then use an antenna to communicate the results to an external reader. The contact lens can also include an energy harvesting system (e.g., a photovoltaic cell or a radio frequency energy-harvesting antenna) to power the measurement and communication electronics. For instance, a control chip may be connected to both the antenna and the sensor, all of which may be disposed on a substrate embedded in the polymeric material of the contact lens. The chip can be configured to: (i) regulate harvested energy from the loop antenna or photovoltaic cell to provide a DC voltage that powers the chip, (ii) operate the sensor to obtain a measurement, and (iii) communicate the measurement using the antenna.

The sensor may be an electrochemical sensor for obtaining measurements of an analyte concentration of the tear fluid. The electrochemical sensor includes a working electrode and a reference electrode (or counter electrode) that are exposed to the tear fluid. During measurement, the working electrode can be charged relative to the reference electrode to generate an amperometric current related to the rate of electrochemical reactions at the working electrode. The sensor electrodes can be formed by patterning conductive material on a substrate using microfabrication techniques. For example, a conductive seed layer can be patterned and then platinum and/or palladium can be electroplated over the seed layer. In some examples, the working electrode may have a width of about 10 micrometers, and the reference electrode can have a surface area exposed to the tear fluid that is several times that of the working electrode. The working electrode and the combination reference-counter electrode can be formed of platinum, palladium, carbon, silver, silver-chloride, gold, other suitable conductive materials, and/or combinations of these.

The contact lens can also include a potentiostat connected to the two electrodes to charge the working electrode with respect to the reference electrode while measuring the current between the two. The working electrode is charged to a voltage sufficient to generate electrochemical reactions at the working electrode with a particular analyte of interest. Those reactions result in an amperometric current between the electrodes due to the analyte being electrochemically consumed at the working electrode. The current thus provides an indication of analyte concentration in the tear fluid. The control electronics also operate the antenna to wirelessly communicate indications of the current.

The present disclosure involves a technique for fabricating electrochemical sensors for such applications. Sensor electrodes for multiple electrochemical sensors can be patterned on a common substrate, such as a silicon wafer, and once the microfabrication process is complete, the substrate can be diced to separate the individual electrochemical sensors. The sensor electrodes are patterned on one side of the substrate, and connection pads are formed on the opposite side of the substrate. Conductive vias through the substrate connect the electrodes to the connection pads. The conductive vias may be formed during the assembly of the sensors by forming an aperture or depression in the substrate and filling it with a conductive material, such as gold. The electrodes can then be patterned and electroplated over the vias, and then the substrate can be flipped over and bonded to a carrier substrate. The reverse side of the sensor substrate can then be polished to a desired thickness and the conductive pads can be patterned on the reverse side. Thus, the individual electrodes (e.g., working electrode and reference electrode) can be electrically connected to the connection pads.

After dicing, the separated sensors (e.g., sensor electrodes patterned on the diced wafers with electrically connected pads on the reverse side) can be flip-chip bonded to another substrate by matching the conductive pads to corresponding terminals. For example, pick and place processes can be used to manipulate the individual "sensor chips" so they are situated on corresponding mounting terminals on another substrate included in the eye-mountable device. The other substrate may include an antenna and interconnects formed of patterned conductive material to define terminals, and a chip may be electrically connected to interact with both the sensor and the antenna. For instance, solder and/or conductive adhesives may be used to electrically couple the conductive pads to the corresponding terminals.

Because the electrochemical sensor chips can be fabricated separate from the remainder of the electronics in the device, the power harvesting, communication, and sensor control electronics can be formed independently of the fabrication of the electrochemical sensor electrodes. Thus, the substrate on which the other electronics are disposed need not be compliant with temperatures and/or solvents used in the microfabrication of the sensor itself. In addition, the fabrication of the electrochemical sensor can be performed in bulk in which a large number of sensors are fabricated on one sensor substrate. This can beneficially reduce the cost of producing the sensors. In one example, over 100,000 sensor chips can be fabricated using a single 12 inch silicon wafer.

An example fabrication process may involve forming depressions in a silicon or glass substrate using deep reactive-ion etching, or a laser, or another technique. The depressions may penetrate the substrate to a given depth, and then the substrate can be thinned. As a result of the thinning, the depressions penetrate through substrate. The depressions can be filled with conductive material to create vias. In one example, a seed layer may be patterned over the depressions to coat the sidewalls thereof, and then gold may be electroplated to a desired thickness. The substrate can then be polished to provide a smooth surface on which to pattern electrodes. Sets of electrodes (e.g., working and reference electrodes) can be patterned on the polished surface. The electrodes can be patterned such that each working electrode and each reference electrode are electrically connected to one of the vias, for example, by overlapping a depression filled by the polished conductive material). After patterning the electrodes, the substrate can be flipped and adhered to a carrier substrate to allow for further processing of the reverse side of the substrate. The reverse side of the substrate can be thinned, by polishing to a desired thickness. Thinning the substrate from the reverse side also exposes the conductive material in the depressions. Conductive material can then be patterned and/or electroplated to create connection pads on the reverse side of the thinned substrate. The sensor substrate can then be detached from the carrier and diced to separate the individual sensor chips.

If the substrate used is a silicon wafer, the substrate may be coated with silicon dioxide or silicon nitride or another insulator prior to applying conductive materials (e.g., electrodes, vias). The coating can thereby passivate the silicon wafer and help ensure that the silicon wafer material does not provide an electrical path between the conductive elements.

In addition, one or both electrodes may be at least partially coated with another passivation layer (e.g., silicon dioxide or silicon nitride) to control the amount of surface area of each electrode that is exposed to fluid. For instance, the working electrode may be patterned to a width of 10 micrometers. A passivation layer may then be applied to cover all but a narrow strip of the working electrode (or a narrow strip of the passivation layer can be etched away to expose only that region of the electrode). As a result, the exposed area of the working electrode may have a width on the order of a single micrometer or perhaps nanometers.

II. Example Body-Mountable Electronics Platform

FIG. 1 is a block diagram of a system 100 that includes a body-mountable device 110 in wireless communication with an external reader 180. The body-mountable device 110 is made of a polymeric material 120 formed to be mounted to a body surface. For instance, the polymeric material 120 may be formed to be contact-mounted to a corneal surface of an eye. A substrate 130 is embedded in the polymeric material 120 to provide a mounting location for electronic components such as a power supply 140, a controller 150, bio-interactive electronics 160, and a communication antenna 170. The bio-interactive electronics 160 are operated by the controller 150. The power supply 140 supplies operating voltages to the controller 150 and/or the bio-interactive electronics 160. The antenna 170 is operated by the controller 150 to communicate information to and/or from the body-mountable device 110. The antenna 170, the controller 150, the power supply 140, and the bio-interactive electronics 160 can all be situated on the embedded substrate 130. In applications in which the body-mountable device is arranged to be contact-mounted to an eye, similar to a contact lens, it may also be referred to herein as an ophthalmic electronics platform.

A. Polymeric Material

The polymeric material 120 can be shaped to include an external surface that is configured to interface with a desired body-mounting location. For example, the polymeric material 120 may include a tooth-mountable surface, a head-mountable surface, an ear-mountable surface, a skin-mountable surface, an eye-mountable surface, and so on. The polymeric material 120 may also be formed to facilitate use as an implantable device. For example, the polymeric material may be smooth and include a bio-compatible coating suitable for applications in which the device 110 is implanted under or within the skin. The body-mountable device 110 may also be implemented in a form factor configured to be mounted to other body locations so as to access sample fluids in-vivo, including implantable configurations. The body-mountable device 110 may therefore include an encapsulating bio-compatible polymeric material 120 in which electronics are embedded, and which includes one or more mounting surfaces. In some examples, the body-mountable device 110 may include a mounting surface configured to be mounted to a tooth, a skin surface, a mucous membrane, upon a subcutaneous region, within an interstitial region, or in another region in which in-vivo fluid analyte concentrations may be measured.

To facilitate contact-mounting to an eye, the polymeric material 120 can have a concave surface configured to adhere ("mount") to a moistened corneal surface (e.g., by capillary forces with a tear film coating the corneal surface). Additionally or alternatively, the body-mountable device 110 can be adhered by a vacuum force between the corneal surface and the polymeric material due to the concave curvature. While mounted with the concave surface against the eye, the outward-facing surface of the polymeric material 120 can have a convex curvature that is formed to not interfere with eye-lid motion while the body-mountable device 110 is mounted to the eye. For example, the polymeric material 120 can be a substantially transparent curved polymeric disk shaped similarly to a contact lens.

The polymeric material 120 can include one or more biocompatible materials, such as those employed for use in contact lenses or other ophthalmic applications involving direct contact with the corneal surface. The polymeric material 120 can optionally be formed in part from such biocompatible materials or can include an outer coating with such biocompatible materials. The polymeric material 120 can include materials configured to moisturize the corneal surface, such as hydrogels and the like. In some embodiments, the polymeric material 120 can be a deformable ("non-rigid") material to enhance wearer comfort. In some embodiments, the polymeric material 120 can be shaped to provide a predetermined, vision-correcting optical power (e.g., for vision correction applications).

B. Substrate

The substrate 130 includes one or more surfaces suitable for mounting the bio-interactive electronics 160, the controller 150, the power supply 140, and the antenna 170. The substrate 130 can be employed both as a mounting platform for chip-based circuitry (e.g., by flip-chip mounting to conductive terminals patterned on the substrate 130) and/or as a platform for patterning conductive materials (e.g., gold, platinum, palladium, titanium, copper, aluminum, silver, metals, other conductive materials, combinations of these, etc.) to create electrodes, interconnects, connection pads, antenna, etc. In some examples, substantially transparent conductive materials (e.g., indium tin oxide) can be patterned on the substrate 130 to form circuitry, electrodes, etc. For example, the antenna 170 can be fabricated by forming a pattern of gold or another conductive material on the substrate 130 by deposition, photolithography, electroplating, etc. Similarly, interconnects 151, 157 between the controller 150 and the bio-interactive electronics 160, and between the controller 150 and the antenna 170, respectively, can be formed by depositing suitable patterns of conductive materials on the substrate 130. A combination of microfabrication techniques including, without limitation, the use of photoresists, masks, deposition techniques, and/or electroplating techniques can be employed to pattern such materials on the substrate 130.

The substrate 130 can be a relatively rigid material, such as polyethylene terephthalate ("PET") or another material configured to structurally support the circuitry and/or chip-based electronics within the polymeric material 120. The body-mountable device 110 can alternatively be arranged with a group of unconnected substrates rather than a single substrate. For example, the controller 150 and a sensor included in the bio-interactive electronics 160 can be mounted to one substrate, while the antenna 170 is mounted to another substrate and the two can be electrically connected via the interconnects 157. In another example, the substrate 130 can include separate partitions that each support separated, overlapped coiled portions of the antenna 170. Such as, for instance, an embodiment in which the antenna 170 is divided into multiple windings that wrap around the body-mountable device 110 circumferentially at respective radii, and are connected in parallel and/or in series. To facilitate movement of the individual windings with respect to one another, and thereby enhance flexibility of the body-mountable device 110, and help prevent binding or other deformation of the antenna, the individual windings may each be mounted on divided portions of the substrate 130.

In an eye-mountable application, the substrate 130 (and the bio-interactive electronics 160 thereon) can be positioned away from the center of the device 110 through which light is transmitted to the pupil. As such, the substrate 130 can avoid interference with light transmission to the central, light-sensitive region of the eye. For example, where the eye-mountable device 110 is shaped as a concave-curved disk, the substrate 130 can be embedded around the periphery (e.g., near the outer circumference) of the disk. In some examples, however, the bio-interactive electronics 160 (and the substrate 130) can be positioned in or near the central region of the eye-mountable device 110. Additionally or alternatively, the bio-interactive electronics 160 and/or substrate 130 can be substantially transparent to incoming visible light to mitigate interference with light transmission to the eye. Moreover, in some embodiments, the bio-interactive electronics 160 can include a pixel array 164 that emits and/or transmits light to be received by the eye according to display instructions. Thus, the bio-interactive electronics 160 can optionally be positioned so as to generate perceivable visual cues to a wearer of an eye-mountable device, such as by displaying information (e.g., characters, symbols, flashing patterns, etc.) on the pixel array 164.

The dimensions of the substrate 130 can depend on a variety of factors. For instance, in an eye-mountable application, the substrate 130 can be shaped as a flattened ring with a radial width dimension sufficient to provide a mounting platform for the embedded electronics components. The substrate 130 can have a thickness sufficiently small to allow the substrate 130 to be embedded in the polymeric material 120 without influencing the profile of the eye-mountable device. The substrate 130 can have a thickness sufficiently large to provide structural stability suitable for supporting the electronics mounted thereon. For example, the substrate 130 may be shaped as a ring with a diameter of about 10 millimeters, a radial width of about 1 millimeter (e.g., an outer radius 1 millimeter larger than an inner radius), and a thickness of about 50 micrometers. The substrate 130 may be shaped along the surface of an imaginary cone between two circular rings that define an inner radius and an outer radius. In such an example, the surface of the substrate 130 along the surface of the imaginary cone defines an inclined surface that is approximately aligned with the curvature of the eye mounting surface at that radius.

C. Power Supply

The power supply 140 is configured to harvest ambient energy to power the controller 150 and bio-interactive electronics 160. For example, a radio-frequency energy-harvesting antenna 142 can capture energy from incident radio radiation. Additionally or alternatively, solar cell(s) 144 ("photovoltaic cells") can capture energy from incoming ultraviolet, visible, and/or infrared radiation. Furthermore, an inertial power scavenging system can be included to capture energy from motion of the body-mountable device 110. The energy harvesting antenna 142 can optionally be a dual-purpose antenna that is also used to communicate information to the external reader 180. That is, the functions of the communication antenna 170 and the energy harvesting antenna 142 can be accomplished with the same physical component(s).

A rectifier/regulator 146 can be used to condition the captured energy to a stable DC supply voltage 141 that is supplied to the controller 150. For example, the energy harvesting antenna 142 can receive incident radio frequency radiation. Varying electrical signals on the leads of the antenna 142 are output to the rectifier/regulator 146. The rectifier/regulator 146 rectifies the varying electrical signals to a DC voltage and regulates the rectified DC voltage to a level suitable for operating the controller 150. Additionally or alternatively, output voltage from the solar cell(s) 144 can be regulated to a level suitable for operating the controller 150. The rectifier/regulator 146 can include one or more energy storage devices to mitigate high frequency variations in the ambient energy gathering antenna 142 and/or solar cell(s) 144. For example, one or more energy storage devices (e.g., a capacitor, an inductor, etc.) can be connected in parallel across the outputs of the rectifier 146 to regulate the DC supply voltage 141 and configured to function as a low-pass filter.

D. Controller and Bio-Interactive Electronics

The controller 150 can be turned on when the DC supply voltage 141 is provided to the controller 150, and the logic in the controller 150 operates the bio-interactive electronics 160 and the antenna 170. The controller 150 can include logic circuitry configured to operate the bio-interactive electronics 160 so as to interact with a biological environment of the body-mountable device 110. The interaction could involve the use of one or more components, such as an analyte bio-sensor 162, in bio-interactive electronics 160 to obtain input from the biological environment. Additionally or alternatively, the interaction could involve the use of one or more components, such as pixel array 164, to provide an output to the biological environment.

In one example, the controller 150 includes a sensor interface module 152 that is configured to operate analyte bio-sensor 162. The analyte bio-sensor 162 can be, for example, an amperometric electrochemical sensor that includes a working electrode and a reference electrode. A voltage can be applied between the working and reference electrodes to cause an analyte to undergo an electrochemical reaction (e.g., a reduction and/or oxidation reaction) at the working electrode. The electrochemical reaction generates an amperometric current that can be measured through the working electrode. The amperometric current is related to the reaction rate, which is related to the analyte concentration. Thus, the amperometric current that is measured through the working electrode can provide an indication of analyte concentration. In some embodiments, the sensor interface module 152 can be a potentiostat configured to apply a voltage between working and reference electrodes while measuring a current through the working electrode.

In some instances, a reagent can also be included to sensitize the electrochemical sensor to one or more desired analytes. For example, a layer of glucose oxidase ("GOx") proximal to the working electrode can catalyze glucose oxidation to generate hydrogen peroxide ($H_2O_2$). The hydrogen peroxide can then be electrooxidized at the working electrode, which releases electrons to the working electrode, resulting in an amperometric current that can be measured through the working electrode. These reactions are shown below.

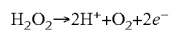

The current generated by either reduction or oxidation reactions is approximately proportionate to the reaction rate. Further, the reaction rate is dependent on the rate of analyte molecules reaching the electrochemical sensor electrodes to fuel the reduction or oxidation reactions, either directly or catalytically through a reagent. In a steady state, where analyte molecules diffuse to the electrochemical sensor electrodes from a sampled region at approximately the same rate that additional analyte molecules diffuse to the sampled region from surrounding regions, the reaction rate is approximately proportionate to the concentration of the analyte molecules. The current measured through the working electrode thus provides an indication of the analyte concentration.

The controller 150 can optionally include a display driver module 154 for operating a pixel array 164. The pixel array 164 can be an array of separately programmable light transmitting, light reflecting, and/or light emitting pixels arranged in rows and columns. The individual pixel circuits can optionally include liquid crystal technologies, microelectromechanical technologies, emissive diode technologies, etc. to selectively transmit, reflect, and/or emit light according to information from the display driver module 154. Such a pixel array 164 can also optionally include more than one color of pixels (e.g., red, green, and blue pixels) to render visual content in color. The display driver module 154 can include, for example, one or more data lines providing programming information to the separately programmed pixels in the pixel array 164 and one or more addressing lines for setting groups of pixels to receive such programming information. Such a pixel array 164 situated on the eye can also be associated with one or more lenses to direct light from the pixel array to a focal plane perceivable by the eye.

The controller 150 can also include a communication circuit 156 for sending and/or receiving information via the antenna 170. The communication circuit 156 can optionally include one or more oscillators, mixers, frequency injectors, etc. to modulate and/or demodulate information on a carrier frequency to be transmitted and/or received by the antenna 170. In some examples, the body-mountable device 110 is configured to indicate an output from a bio-sensor by modulating an impedance of the antenna 170 in a manner that is perceivable by the external reader 180. For example, the communication circuit 156 can cause variations in the amplitude, phase, and/or frequency of backscatter radiation from the antenna 170, and such variations can be detected by the reader 180.

The controller 150 is connected to the bio-interactive electronics 160 via interconnects 151. For example, where the controller 150 includes logic elements implemented in an integrated circuit to form the sensor interface module 152 and/or display driver module 154, a patterned conductive material (e.g., gold, platinum, palladium, titanium, copper, aluminum, silver, metals, combinations of these, etc.) can connect a terminal on the chip to the bio-interactive electronics 160. Similarly, the controller 150 is connected to the antenna 170 via interconnects 157.

It is noted that the block diagram shown in FIG. 1 is described in connection with functional modules for convenience in description. However, embodiments of the body-mountable device 110 can be arranged with one or more of the functional modules ("sub-systems") implemented in a single chip, integrated circuit, and/or physical component. For example, while the rectifier/regulator 146 is illustrated in the power supply block 140, the rectifier/regulator 146 can be implemented in a chip that also includes the logic elements of the controller 150 and/or other features of the embedded electronics in the body-mountable device 110. Thus, the DC supply voltage 141 that is provided to the controller 150 from the power supply 140 can be a supply voltage that is provided to components on a chip by rectifier and/or regulator components located on the same chip. That is, the functional blocks in FIG. 1 shown as the power supply block 140 and controller block 150 need not be implemented as physically separated modules. Moreover, one or more of the functional modules described in FIG. 1 can be implemented by separately packaged chips electrically connected to one another.

Additionally or alternatively, the energy harvesting antenna 142 and the communication antenna 170 can be implemented with the same physical antenna. For example, a loop antenna can both harvest incident radiation for power generation and communicate information via backscatter radiation.

E. Reader

The external reader 180 includes an antenna 188 (or a group of multiple antennas) to send and receive wireless signals 171 to and from the body-mountable device 110. The external reader 180 also includes a computing system with a processor 186 in communication with a memory 182. The memory 182 can be a non-transitory computer-readable medium that can include, without limitation, magnetic disks, optical disks, organic memory, and/or any other volatile (e.g. RAM) or non-volatile (e.g. ROM) storage system readable by the processor 186. The memory 182 can include a data storage 183 to store indications of data, such as sensor readings (e.g., from the analyte bio-sensor 162), program settings (e.g., to adjust behavior of the body-mountable device 110 and/or external reader 180), etc. The memory 182 can also include program instructions 184 for execution by the processor 186 to cause the external reader 180 to perform processes specified by the instructions 184. For example, the program instructions 184 can cause external reader 180 to provide a user interface that allows for retrieving information communicated from the body-mountable device 110 (e.g., sensor outputs from the analyte bio-sensor 162). The external reader 180 can also include one or more hardware components for operating the antenna 188 to send and receive the wireless signals 171 to and from the body-mountable device 110. For example, oscillators, frequency injectors, encoders, decoders, amplifiers, filters, etc. can drive the antenna 188 according to instructions from the processor 186.

The external reader 180 can be a smart phone, digital assistant, or other portable computing device with wireless connectivity sufficient to provide the wireless communication link 171. The external reader 180 can also be implemented as an antenna module that can be plugged in to a portable computing device, such as in an example where the communication link 171 operates at carrier frequencies not commonly employed in portable computing devices. In some instances, the external reader 180 is a special-purpose device configured to be worn relatively near a wearer's eye to allow the wireless communication link 171 to operate with a low power budget. For example, the external reader 180 can be integrated in a piece of jewelry such as a necklace, earing, etc. or integrated in an article of clothing or an accessory worn near the head, such as a hat, headband, a scarf, a pair of eyeglasses, etc.

In some embodiments, the system 100 can operate to non-continuously ("intermittently") supply energy to the body-mountable device 110 to power the controller 150 and sensor electronics 160. For example, radio frequency radiation 171 can be supplied to power the body-mountable device 110 long enough to operate the sensor electronics 160 and communicate an outcome of such operation. In such an example, the supplied radio frequency radiation 171 can be considered an interrogation signal from the external reader 180 to the body-mountable device 110 to request feedback (e.g., a sensor measurement). By periodically interrogating the body-mountable device 110 (e.g., by supplying radio frequency radiation 171 to temporarily turn the device on), the external reader 180 can accumulate a set of measurements (or other feedback) over time from the sensor electronics 160 without continuously powering the body-mountable device 110.

F. Example Operation

In practice, the power supply 140 can function to harvest energy from received radio frequency radiation using the energy harvesting antenna 142 and the rectifier/regulator 146. For example, radio frequency radiation can cause radio frequency electrical signals on leads of the antenna 142. The rectifier 146 can be connected to the antenna leads and convert the radio frequency electrical signals to a DC voltage. An energy storage device (e.g., a capacitor) can be connected across the output of the rectifier 146 to filter out high frequency components of the DC voltage from the rectifier. A voltage regulator can then receive the DC voltage and output supply voltages (i.e., the DC power 141) to operate the hardware logic of the controller 150 and also to power the electrochemical sensor 162. The DC supply voltage(s) 141 may be voltages suitable for driving digital logic circuitry, such as approximately 1.2 volts, approximately 3 volts, etc. Reception of the radio frequency radiation from the external reader 180 (or another source, such as ambient radiation, etc.) causes the supply voltages 141 to be supplied to the sensor 162 and hardware logic of the controller 150, thereby activating the body-mountable device 110. While powered, the sensor 162 and sensor interface 152 of the controller 150 are configured to generate and measure a current indicative of analyte concentration and communicate the results.

The external reader 180 associates the backscatter signal 171 with the sensor result (e.g., according to a pre-programmed relationship associating impedance of the antenna 170 with output from the sensor 162 using look-up tables, calibration information, etc.). The reader 180 can then store the indicated sensor results (e.g., analyte concentration values) in a local memory and/or an external data storage (e.g., by communicating through a network).

In some embodiments, one or more of the features shown as separate functional blocks can be implemented ("packaged") on a single chip. For example, the body-mountable device 110 can be implemented with a rectifier 146, energy storage, voltage regulator, sensor interface 152, and other hardware logic packaged together in a single chip or controller module. Such a controller can have interconnects ("leads") connected to the loop antenna 170 and a sensor chip on which the analyte bio-sensor 162 is disposed. Such a controller operates to harvest energy received at the loop antenna 170, apply a voltage between the electrodes of the sensor 162 sufficient to develop an amperometric current, measure the amperometric current, and indicate the measured current via the antenna 170 (e.g., through the backscatter radiation 171).

G. Example Eye-Mountable Electronics Platform

Figure 2A:
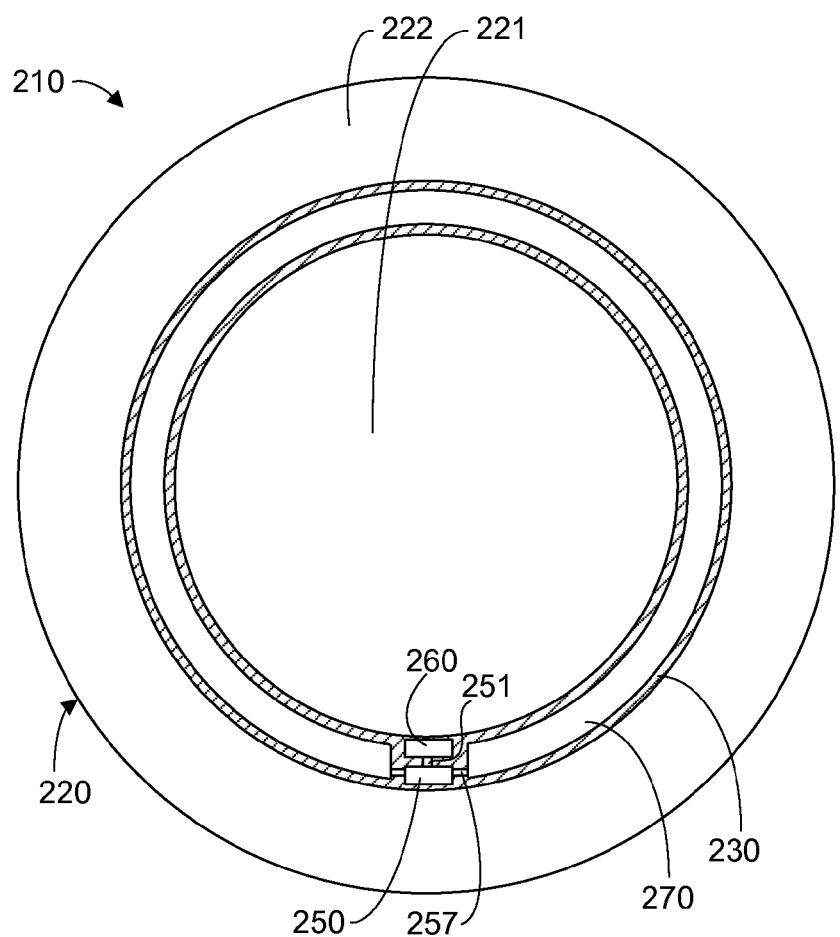
FIG. 2A is a top view of an example eye-mountable device.
Figure 2B:
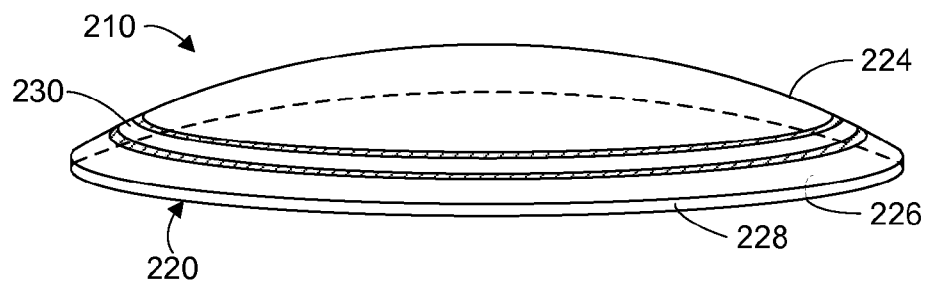
FIG. 2B is a side view of the example eye-mountable device shown in FIG. 2A.

FIG. 2A is a top view of an example eye-mountable electronic device 210 (or ophthalmic electronics platform). FIG. 2B is an aspect view of the example eye-mountable electronic device shown in FIG. 2A. It is noted that relative dimensions in FIGS. 2A and 2B are not necessarily to scale, but have been rendered for purposes of explanation only in describing the arrangement of the example eye-mountable electronic device 210. The eye-mountable device 210 can be formed of a polymeric material 220 shaped as a curved disk. The eye-mountable device 210 includes a loop antenna 270, a controller 250, and an electrochemical sensor 260 mounted on a substrate 230 that is embedded in the polymeric material 220.

The polymeric material 220 can be a substantially transparent material to allow incident light to be transmitted to the eye while the eye-mountable device 210 is mounted to the eye. The polymeric material 220 can be a biocompatible material similar to those employed to form vision correction and/or cosmetic contact lenses in optometry, such as polyethylene terephthalate ("PET"), polymethyl methacrylate ("PMMA"), polyhydroxyethylmethacrylate ("polyHEMA"), silicone hydrogels, combinations of these, etc. The polymeric material 220 can be formed with one side having a concave surface 226 suitable to fit over a corneal surface of an eye. The opposite side of the disk can have a convex surface 224 that does not interfere with eyelid motion while the eye-mountable device 210 is mounted to the eye. A circular outer side edge 228 connects the concave surface 226 and convex surface 224. The polymeric material 220 can be formed with a curved shape in a variety of ways. For example, techniques similar to those employed to form vision-correction contact lenses can be employed to form the polymeric material 220, such as heat molding, injection molding, spin casting, etc.

The eye-mountable device 210 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 210 can be selected according to the size and/or shape of the corneal surface of the wearer's eye and/or to accommodate one or more components embedded in the polymeric material 220.

While the eye-mountable device 210 is mounted in an eye, the convex surface 224 faces outward to the ambient environment while the concave surface 226 faces inward, toward the corneal surface. The convex surface 224 can therefore be considered an outer, top surface of the eye-mountable device 210 whereas the concave surface 226 can be considered an inner, bottom surface. The "top" view shown in FIG. 2A is facing the convex surface 224.

The substrate 230 can be embedded in the polymeric material 220 so as to be situated along the outer periphery 222 of the polymeric material 220, away from the central region 221. The substrate 230 can be shaped as a flat, circular ring (e.g., a disk with a centered hole). The flat surface of the substrate 230 (e.g., along the radial width) serves as a platform for mounting electronics such as chips (e.g., via flip-chip mounting) and for patterning conductive materials (e.g., via microfabrication techniques such as photolithography, deposition, plating, etc.) to form electrodes, antenna(e), and/or interconnections. Both the substrate 230 and the polymeric material 220 can be approximately cylindrically symmetric about a common central axis. The substrate 230 can have, for example, a diameter of about 10 millimeters, a radial width of about 1 millimeter (e.g., an outer radius 1 millimeter greater than an inner radius), and a thickness of about 50 micrometers. However, these dimensions are provided for example purposes only, and in no way limit the present disclosure. The substrate 230 can be implemented to assume a variety of different form factors, similar to the discussion of the substrate 130 in connection with FIG. 1 above.

The controller 250 can be a chip including logic elements configured to operate the electrochemical sensor 260 and the loop antenna 270. The controller 250 is electrically connected to the loop antenna 270 by interconnects 257 also situated on the substrate 230. Similarly, the controller 250 is electrically connected to the sensor 260 by an interconnect 251. The interconnects 251, 257, the loop antenna 270, and conductive electrodes included in the sensor 260 can be formed from conductive materials patterned on the substrate 230 by a process for precisely patterning such materials, such as deposition, photolithography, etc. The conductive materials patterned on the substrate 230 can be, for example, gold, platinum, palladium, titanium, carbon, aluminum, copper, silver, silver-chloride, conductors formed from noble materials, metals, combinations of these, etc.

The loop antenna 270 is a layer of conductive material patterned along the flat surface of the substrate to form a flat conductive ring. In some examples, to allow additional flexibility along the curvature of the polymeric material, the loop antenna 270 can include multiple substantially concentric sections electrically joined together in parallel or in series. Each section can then flex independently along the concave/convex curvature of the eye-mountable device 210. In some examples, the loop antenna 270 can be formed without making a complete loop. For instances, the antenna 270 can have a cutout to allow room for the controller 250 and the sensor 260, as illustrated in FIG. 2A. However, the loop antenna 270 can also be arranged as a continuous strip of conductive material that wraps entirely around the flat surface of the substrate 230 one or more times. For example, a strip of conductive material with multiple windings can be patterned on the side of the substrate 230 opposite the controller 250 and sensor 260. Interconnects between the ends of such a wound antenna (e.g., the antenna leads) can then be passed through the substrate 230 to the controller 250.

Figure 2D:
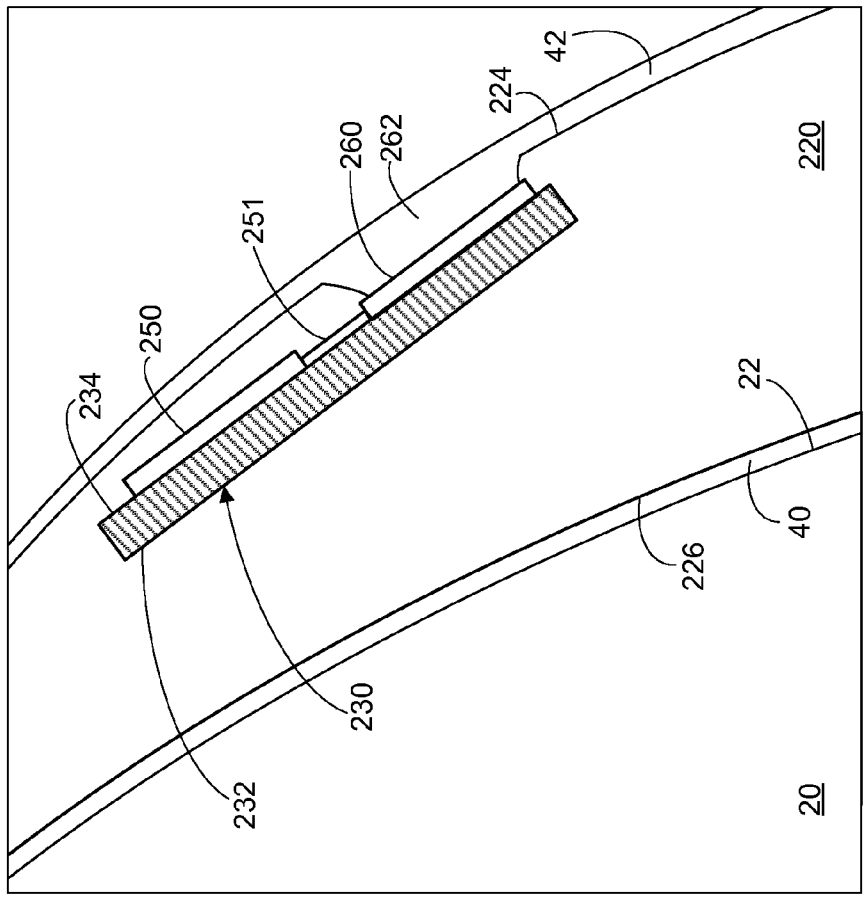
FIG. 2D is a side cross-section view enhanced to show the tear film layers surrounding the surfaces of the example eye-mountable device when mounted as shown in FIG. 2C.
Figure 2C:
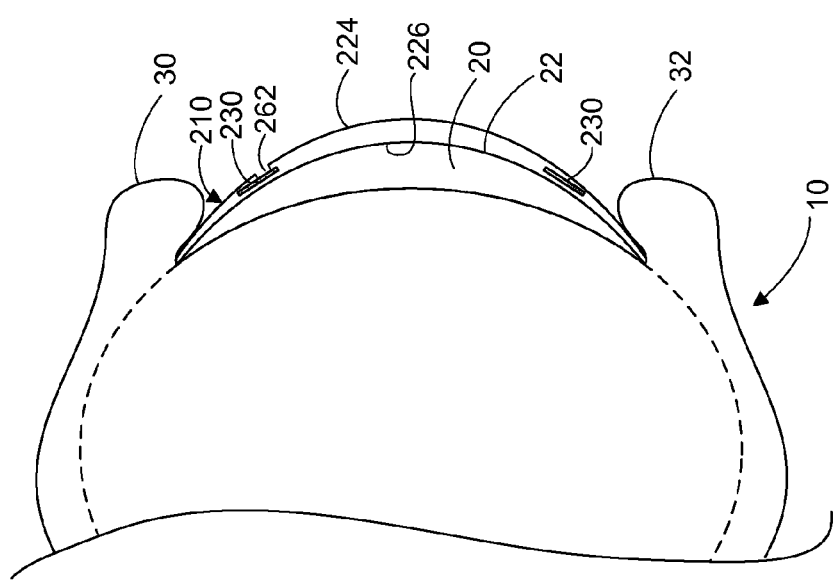
FIG. 2C is a side cross-section view of the example eye-mountable device shown in FIGS. 2A and 2B while mounted to a corneal surface of an eye.

FIG. 2C is a side cross-section view of the example eye-mountable electronic device 210 while mounted to a corneal surface 22 of an eye 10. FIG. 2D is a close-in side cross-section view enhanced to show the tear film layers 40, 42 surrounding the exposed surfaces 224, 226 of the example eye-mountable device 210. It is noted that relative dimensions in FIGS. 2C and 2D are not necessarily to scale, but have been rendered for purposes of explanation only in describing the arrangement of the example eye-mountable electronic device 210. For example, the total thickness of the eye-mountable device can be about 200 micrometers, while the thickness of the tear film layers 40, 42 can each be about 10 micrometers, although this ratio may not be reflected in the drawings. Some aspects are exaggerated to allow for illustration and to facilitate explanation.

The eye 10 includes a cornea 20 that is covered by bringing the upper eyelid 30 and lower eyelid 32 together over the top of the eye 10. Incident light is received by the eye 10 through the cornea 20, where light is optically directed to light-sensing elements of the eye 10 (e.g., rods and cones, etc.) to stimulate visual perception. The motion of the eyelids 30, 32 distributes a tear film across the exposed corneal surface 22 of the eye 10. The tear film is an aqueous solution secreted by the lacrimal gland to protect and lubricate the eye 10. When the eye-mountable device 210 is mounted in the eye 10, the tear film coats both the concave and convex surfaces 224, 226 with an inner layer 40 (along the concave surface 226) and an outer layer 42 (along the convex layer 224). The tear film layers 40, 42 can be about 5 to 10 micrometers in thickness and together account for about 5 to 10 microliters.

The tear film layers 40, 42 are distributed across the corneal surface 22 and/or the convex surface 224 by motion of the eyelids 30, 32. For example, the eyelids 30, 32 may raise and lower, respectively, to spread a small volume of tear film across the corneal surface 22 and/or the convex surface 224 of the eye-mountable device 210. The tear film layer 40 on the corneal surface 22 also facilitates mounting the eye-mountable device 210 by capillary forces between the concave surface 226 and the corneal surface 22.

As shown in the cross-sectional views in FIGS. 2C and 2D, the substrate 230 can be inclined such that the flat mounting surfaces of the substrate 230 are approximately parallel to an adjacent portion of the convex surface 224. The substrate 230 can be a flattened ring with an inward-facing surface 232 (closer to the concave surface 226 of the polymeric material 220) and an outward-facing surface 234 (closer to the convex surface 224). The substrate 230 can have electronic components and/or patterned conductive materials mounted to either or both mounting surfaces 232, 234. As shown in FIG. 2D, the electrochemical sensor 260, controller 250, and conductive interconnect 251 are mounted on the outward-facing surface 234. However, the electronics, electrodes, etc. situated on the substrate 230 can be mounted to either the "inward" facing side 232 or the "outward" facing side 234. Moreover, in some embodiments, some electronic components can be mounted on one side (e.g., 232), while other electronic components are mounted to the opposing side (e.g., 234), and connections between the two sides can be made through conductive materials passing through the substrate 230.

The electrochemical sensor 260 includes two electrodes (e.g., a working electrode and a reference electrode). The electrochemical sensor 260 is exposed to tear film 42 coating the outer convex surface 224 by channel 262. The electrochemical sensor 260 may be implemented as an electrochemical sensor chip that is disposed on a sensor substrate separate from the substrate 230. The electrochemical sensor chip can have electrodes patterned on one side, and each electrode can be connected to a conductive pad on the reverse side of the sensor substrate. Such an electrochemical sensor chip can then be mounted over corresponding conductive pads formed on the substrate 230 when the sensor chip is positioned on the substrate 230.

The electrochemical sensor is connected to the controller 250 via the interconnect 251. The controller 250 can use the electrochemical sensor 260 to obtain measurements of tear film analyte concentration by applying a voltage to the electrodes of the electrochemical sensor 260 and monitoring the resulting amperometric current through the working electrode. The controller 250 can then use the antenna 270 to indicate the measured current.

H. Example Electrochemical Sensor Electrode Arrangement

Figure 3:
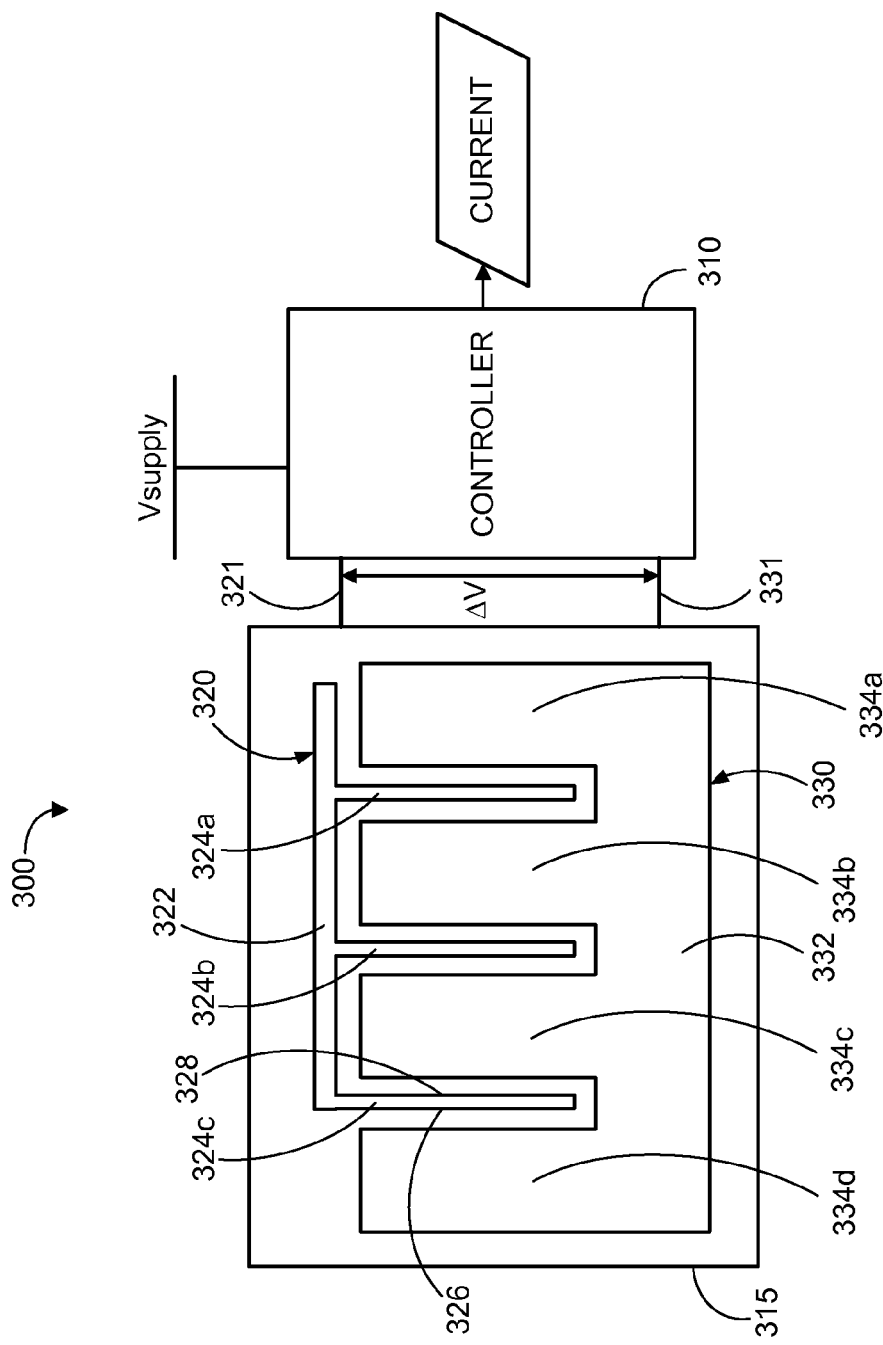
FIG. 3 illustrates an example electrochemical analyte sensor.

FIG. 3 illustrates one example arrangement for electrodes in an electrochemical sensor 300. The arrangement illustrated by FIG. 3 is not drawn to scale, but instead is provided for explanatory purposes to describe an example arrangement of sensor electrodes, which may be implemented with any of the electrochemical sensor electrodes described herein. The electrochemical sensor 300 can be included in an eye-mountable device for detecting a tear film concentration of an analyte (e.g., the eye-mountable device 210 described in connection with FIGS. 2A-2D above), or in a body-mountable or implantable device. The electrochemical sensor 300 includes a working electrode 320 and a reference electrode 330 disposed on a substrate 315.

The electrodes 320, 330 are each electrically coupled to a controller 310 which operates the sensor 300 by applying a voltage $\Delta V$ between the working electrode 320 and the reference electrode 330. The controller 310 is electrically coupled to the working electrode 320 by a conductive interconnect 321; and the controller 310 is electrically coupled to the reference electrode 330 by a conductive interconnect 331. The voltage $\Delta V$ can be a reduction voltage sufficient to cause a reduction reaction at the working electrode 320 involving an analyte of interest. Such a reduction reaction releases electrons from the working electrode 320 and thereby generates an amperometric current that can be measured through the working electrode 320. Additionally or alternatively, the voltage $\Delta V$ can be an oxidization voltage sufficient to cause an oxidization reaction at the working electrode 320 involving the analyte of interest. The oxidation reaction contributes electrons to the working electrode 320 and thereby generates an amperometric current that can be measured through the working electrode 320. The controller 310 is powered by a supply voltage Vsupply and outputs an indication of the amperometric current. In some embodiments, the controller 310 may include a potentiostat. In some examples, the substrate 315 on which the electrodes 320, 330 are disposed may be distinct from a substrate on which the controller 310 is disposed. Thus, the electrodes 320, 330 may be disposed on a sensor substrate 315 (or sensor chip) and can be connected to the interconnects 321, 331 through respective vias and mounting pads on the reverse side of the substrate 315.

The working electrode 320 includes a base 322 from which finger extensions 324a-c extend. The reference electrode 330 includes a base 332 from which finger extensions 334a-d extend. The working electrode 320 and the reference electrode 330 can be arranged such that finger extensions 324a-c and 334a-d of the two electrodes 320, 330 are interdigitated with one another. In some examples, the sensor electrodes 320, 330 can be at least approximately co-planar (e.g., disposed on a common substrate). In some examples, the extensions 324a-c, 334a-d can each extend at least approximately perpendicular to the respective bases 322, 332 of the sensor electrodes. In some examples, the extensions 324a-c, 334a-d can extend at least approximately in parallel with one another. In some examples, the extensions 324a-c of the working electrode 320 can be at least approximately equidistant from nearest ones of the reference electrode extensions 334a-d, along the side edges of each extension 324a-c.

In some examples, each of the extensions 324a-c of the working electrode 320 are at least partially surrounded on opposing sides by two of the extensions 334a-d of the reference electrode 330. For example, the extension 324c of the working electrode extends from the base 322 from a point near the base 322 to a distal end. The extension 324c includes a first side edge 326 and a second side edge 328 opposite the first side. The first and second side edges 326, 328 define the width of the extension 324c. The first side edge 326 of the working electrode extension 324c is adjacent one extension 334d of the reference electrode, and the second side edge 328 is adjacent another extension 334c of the reference electrode. The inter-electrode spacing between the extension 324c and the two reference electrode extensions 334c, 334d (e.g., the gap between the first side edge 326 and the extension 334d and the gap between the second side edge 328 and the extension 334c) can be similar along both side edges 326, 328. For example, both sides can have an approximately uniform gap distance. In another example, both sides can have a tapered (or other varying) gap distance that varies symmetrically between the base 322 and the distal end of the extension 324c. As a result of the symmetric arrangement, the voltage potential is similar along both side edges 326, 328 of the working electrode extension 324c while a voltage is applied across the sensor electrodes 320, 330. The remaining working electrode extensions 324a-b can be similarly situated with opposing side edges adjacent extensions of the reference electrode 330. That is, the working electrode extension 324b is symmetrically surrounded by the reference electrode extensions 334c and 334b, and the working electrode extension 324a is symmetrically surrounded by the reference electrode extensions 334b and 334a.

In some embodiments, at least one of the dimensions of the working electrode 320, such as a width of one or more of the extensions 324a-c, can be less than 100 micrometers. In some embodiments, the working electrode 320 is a microelectrode with at least one dimension of about 25 micrometers. In some cases, the working electrode 320 can have a width of about 10 micrometers, or a width (or other dimension) between 10 and 100 micrometers. The reference electrode 330 can have an exposed area that is about five times larger than the exposed area of the working electrode 320. In some examples, a width of the reference electrode extensions 334a-d can be approximately five times larger than the width of the working electrode extensions 324a-c. Thus, the reference electrode extensions 334a-d may have a width of about 125 micrometers and the working electrode extensions 324a-c may have a width of about 25 micrometers. Many other example dimensions are also possible.

The length of the working electrode extensions 324a-c (e.g., distance between the base 322 and the distal end of each extension) can be selected to provide a desired total cumulative length of all working electrode extensions 324a-c. As noted above, the sensitivity of the electrochemical sensor 320 is determined, at least in part, by the number of induced electrochemical reactions involving an analyte that occur upon exposing the analyte to the sensor electrodes 320, 330. Because electrochemical reactions are induced preferentially along the side edges of the working electrode 320 adjacent to respective sections of the working electrode 330, where the local voltage gradient is greatest (e.g., along the side edges 326, 328 of the extension 324c, and the side edges of the other extensions 324a-b), the sensitivity of the electrochemical sensor 300 depends, at least in part, on the total length of such side edges. In some embodiments, desired sensor sensitivity may be achieved by configurations having a total cumulative length of working electrode extensions of about 1000 micrometers. In such a symmetric configuration, the total length of working electrode side edges situated adjacent respective portions of the reference electrode is approximately double the total cumulative length (e.g., about 2000 micrometers). Thus, some embodiments may include configurations with a working electrode that has two extensions, each about half of the total desired cumulative length; other embodiments may include configurations with a working electrode that has three extensions (as in FIG. 3), and each may be about a third of the total desired cumulative length. Other cumulative lengths of the working electrode 320 can also be selected to provide a desired total length of working electrode side edges adjacent respective sections of the reference electrode to achieve a desired sensor sensitivity.

The thickness of the sensor electrodes 320, 330 (e.g., height on the substrate 315) can be 1 micrometer or less. The thickness dimension can be, for example, between about 1 micrometer and about 50 nanometers, such as approximately 500 nanometers, approximately 250 nanometers, approximately 100 nanometers, approximately 50 nanometers, etc. In some cases the working electrode 320 can be a conductive material patterned on a substrate to have a width of about 25 micrometers, a length of about 1000 micrometers, and a thickness of about 0.5 micrometers. In some embodiments, the reference electrode 330 can be have a similar thickness and can be larger in total area than the working electrode 320. For example, the reference electrode 330 have an area more than five times greater than the area of the working electrode 320.

The electrodes 320, 330 can each be formed by patterning conductive materials on a substrate (e.g., by deposition techniques, lithography techniques, etc.). The conductive materials can be gold, platinum, palladium, titanium, silver, silver-chloride, aluminum, carbon, metals, conductors formed from noble materials, combinations of these, etc. In some embodiments, the working electrode 320 can be formed substantially from platinum (Pt). In some embodiments, the reference electrode 330 can be formed substantially from silver silver-chloride (Ag/AgCl).

I. Example Operations

Figure 4A:
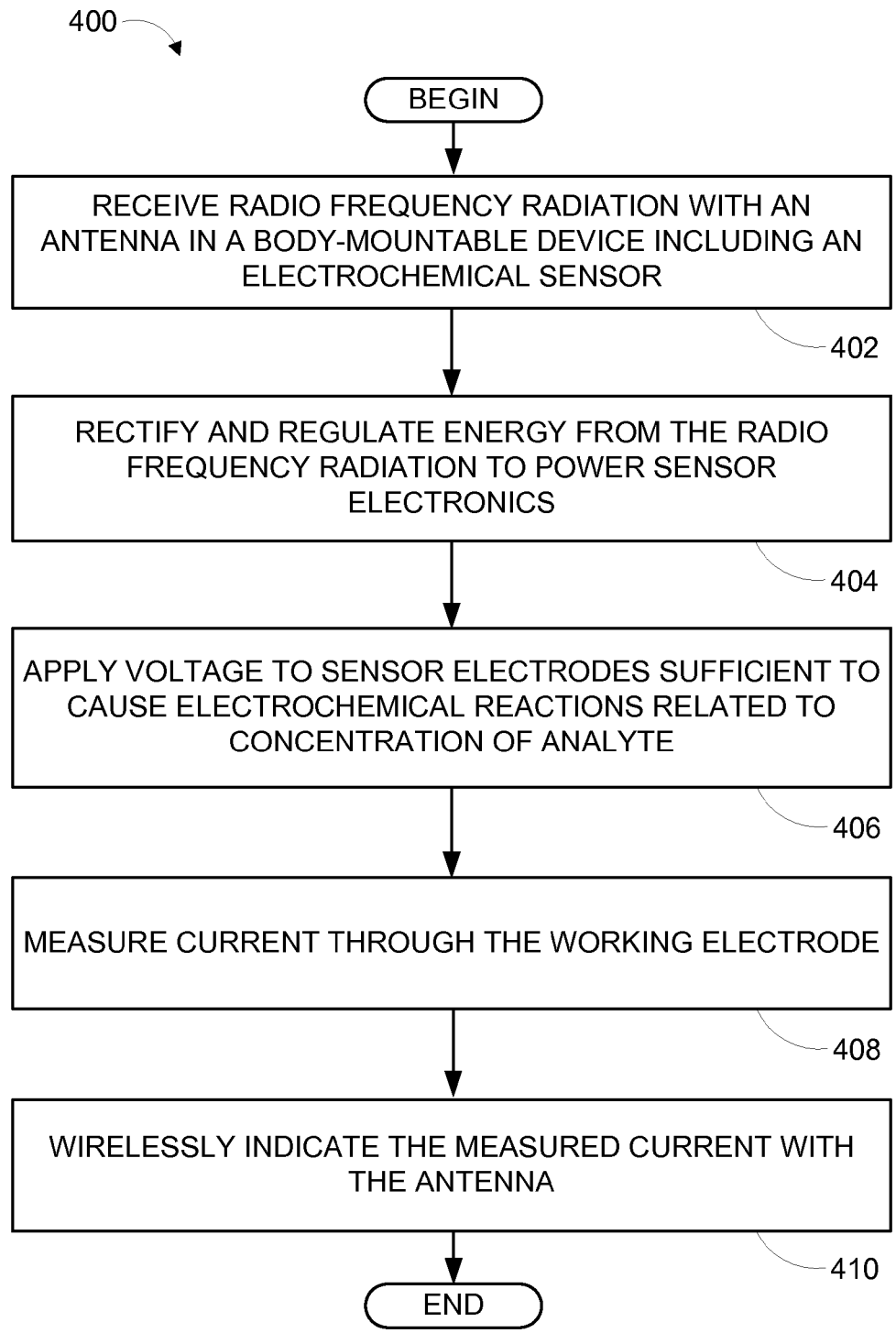
FIG. 4A is a flowchart of an example process for operating a sensor in a body-mountable device to measure analyte concentration.

FIG. 4A is a flowchart of an example process 400 for operating a sensor in a body-mountable device to measure an analyte concentration. Radio frequency radiation is received at an antenna in a body-mountable device including an electrochemical sensor (402). Electrical signals due to the received radiation are rectified and regulated to power the sensor and associated controller (404). For example, a rectifier and/or regulator can be connected to the antenna leads to output a DC supply voltage for powering the sensor, controller, and/or other bio-interactive electronics. A voltage is applied to sensor electrodes sufficient to cause electrochemical reactions at the working electrode (406). For example, a voltage sufficient to induce an oxidation and/or reduction reaction involving the analyte can be applied. The electrochemical reactions generate an amperometric current, and the current is measured through the working electrode (408). For example, a controller may apply the voltage to the electrodes while measuring the amperometric current. The measured current is then wirelessly indicated with the antenna (410). For example, backscatter radiation can be manipulated to indicate the sensor result by modulating the antenna impedance.

Figure 4B:
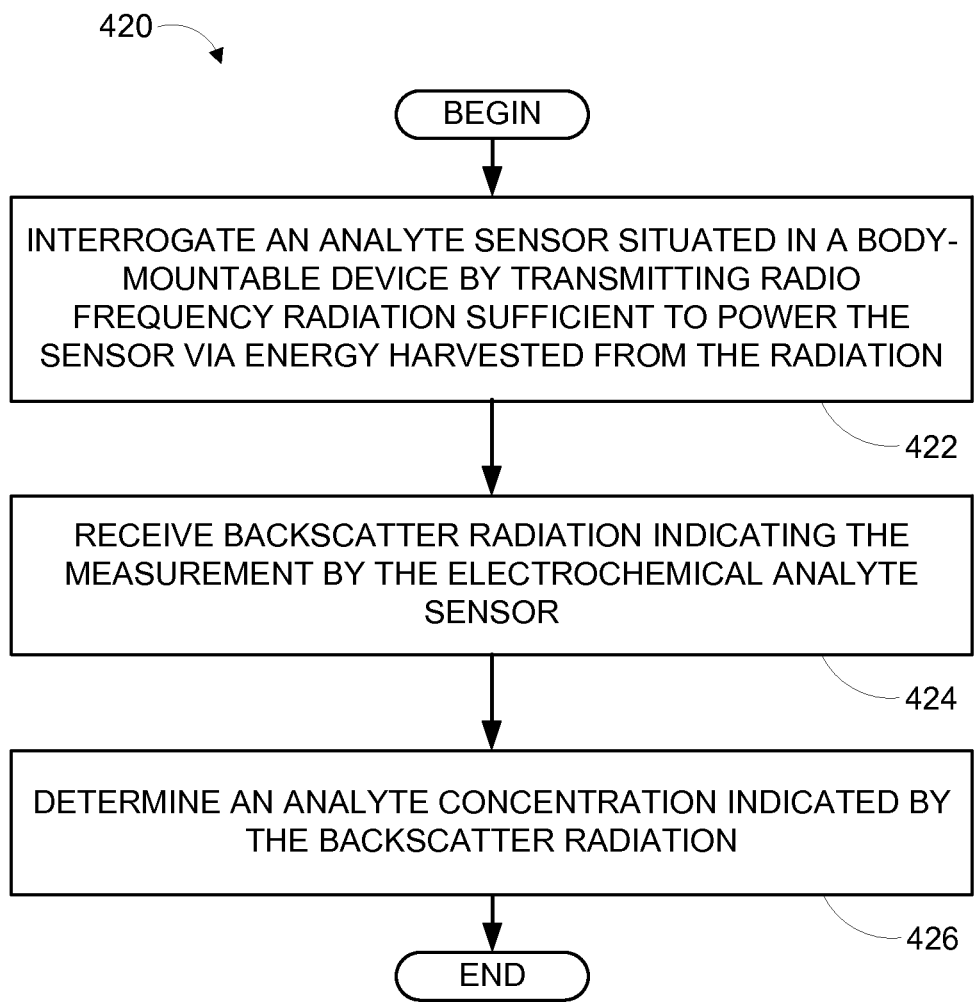
FIG. 4B is a flowchart of an example process for operating an external reader to interrogate an electrochemical sensor in a body-mountable device.

FIG. 4B is a flowchart of an example process 420 for operating an external reader to interrogate a sensor in a body-mountable device. Radio frequency radiation is transmitted from the external reader to an electrochemical sensor included in a body-mountable device (422). The transmitted radiation can be sufficient to power the sensor to perform a measurement and communicate the results. For example, the radio frequency radiation used to power the electrochemical sensor can be similar to the radiation transmitted from the external reader 180 to the body-mountable device 110 described above in connection with FIG. 1. The external reader then receives backscatter radiation from the body-mountable device indicating the measurement by the electrochemical sensor (424). For example, the backscatter radiation can be similar to the backscatter signals 171 sent from the body-mountable device 110 to the external reader 180 described above in connection with FIG. 1. The backscatter radiation received at the external reader is then associated with an analyte concentration value (426). In some cases, the determined analyte concentration value can be stored in the external reader memory and/or a network-connected data storage.

For example, the sensor result (e.g., the measured current) can be encoded in the backscatter radiation by modulating the impedance of the backscattering antenna. The external reader may detect the antenna impedance and/or change in antenna impedance based on a frequency, amplitude, and/or phase shift in the backscatter radiation. The sensor result can then be extracted by associating the impedance value with the sensor result by reversing the encoding routine employed within the eye-mountable device. Thus, the reader can map a detected antenna impedance value to a measured current value. The current value can then be associated with an analyte concentration value based on a look-up table or a predetermined relationship (e.g., a relationship defined in part based on calibration data). In some cases, the determination of an analyte concentration value may account for various factors that influence the scaling between analyte concentration and measured current, including the temperature of the body-mountable device.

III. Electrochemical Sensor Chip

Figure 5A:
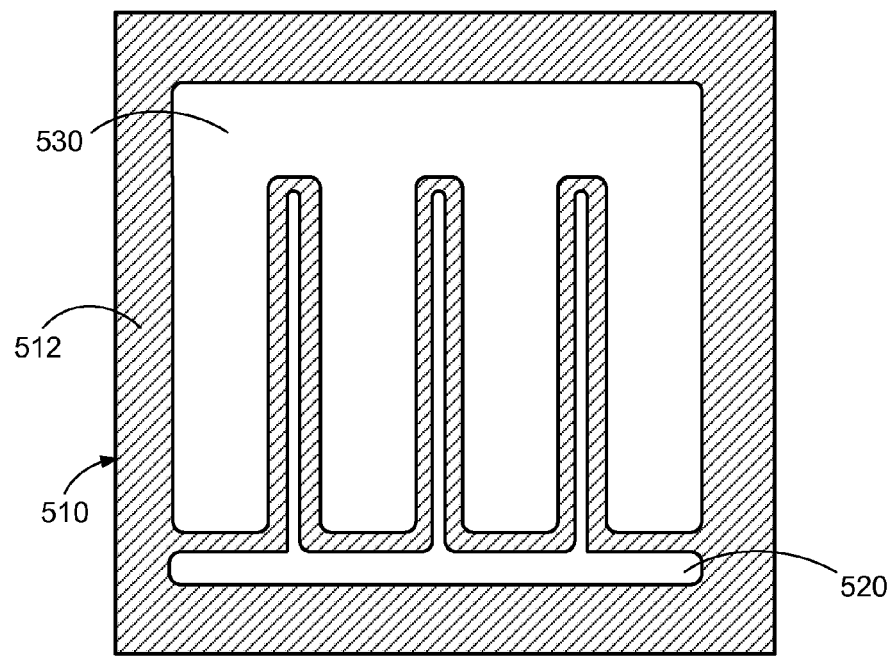
FIG. 5A shows a top view of an example electrochemical sensor chip with electrodes formed on one side.

FIG. 5A shows a top view of an example electrochemical sensor chip 510 with electrodes 520, 530 formed on one side 512. In this example, electrode 520 may function as a working electrode, and electrode 530 may function as a reference and/or counter electrode. In addition, electrode 530 may have a larger surface area than that of electrode 520. For example, the surface area of electrode 530 could be about five times the surface area of electrode 520.

Figure 5B:
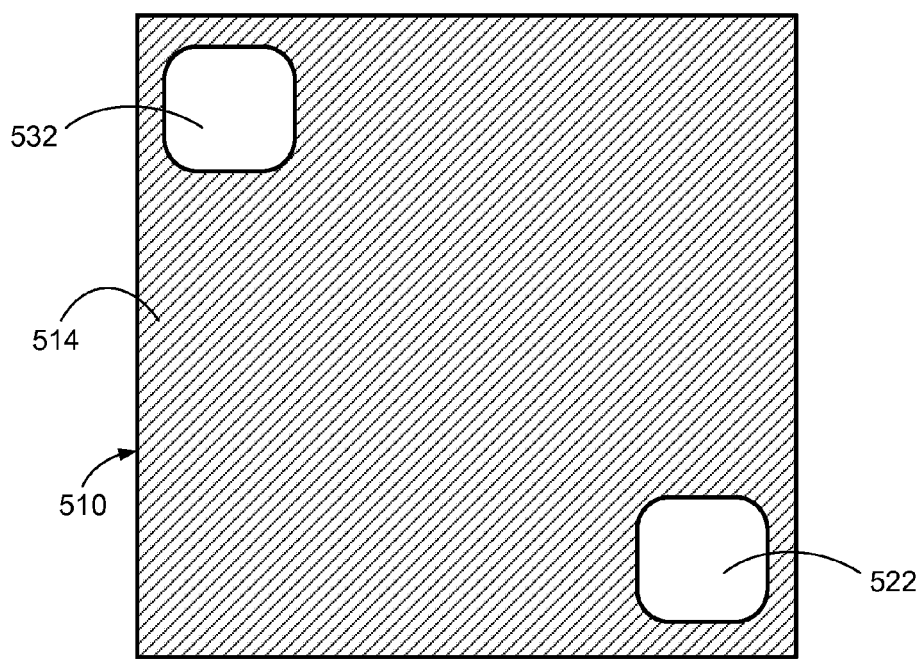
FIG. 5B shows a bottom view of the example electrochemical sensor chip shown in FIG. 5A with conductive pads formed on a reverse side.

FIG. 5B shows a bottom view of the example electrochemical sensor chip shown in FIG. 5A with conductive pads formed on a reverse side 514. The sensor chip 510 can be a substrate, such as silicon or glass with a pair of conductive vias that pass through the substrate. The conductive vias may be, for example, gold or copper electroplated to fill a pair of etched or laser-formed apertures through the substrate.

Electrochemical sensor electrodes 520, 530 can then be patterned on the top side 512, and conductive pads 532, 522 can be patterned on the reverse side 514 of the substrate. For instance, the first conductive pad 532 can be electrically coupled to the reference electrode 530 through a first conductive via; and the second conductive pad 522 can be electrically coupled to the working electrode 520 through a second conductive via. Similar to the sensor electrodes discussed above in connection with FIG. 3, the sensor electrodes 520, 530 can be patterned on the top side 512 using microfabrication techniques, such as patterning a seed layer (e.g., adhesion layer including chromium, titanium, palladium, or another metal) and electroplating another conductive material over the seed layer to form the electrodes 520, 530. The sensor electrodes 520, 530 may be formed of platinum, silver, silver-chloride, or another conductive material.

A range of different sensor chip geometries may be achieved in different embodiments depending on the desired total electrode surface area, the desired total size of the sensor chip 510, the tolerance(s) of various microfabrication processes, and/or other factors. The sensor chip 510 may be square or rectangular with sides between about 500 micrometers and 3000 micrometers in length. Depending on the particular dicing technique, the sensor chip may also have a shape other than square or rectangular. The conductive pads 522, 532 can be formed of gold, copper, or another conductive material to a thickness that extends beyond the reverse surface 514 of the sensor chip 510 by a height between about 1 micrometer and about 10 micrometers. Each of the conductive pads 522, 532 can have a diameter of about 50 micrometers or can occupy a larger area of the reverse surface 514. In some examples, each of the conductive pads 522, 532 may occupy approximately half of the reverse surface 514 to provide a larger surface area to align with conductive terminals when placing the sensor chip 510 during flip-chip bonding. The sensor electrodes 520, 530 may have a thickness between about 100 nanometers and about 500 nanometers. As shown in FIG. 5A, both the working electrode 520 and the reference electrode 530 can include interdigitated extensions, similar to the electrode arrangement described above in connection with FIG. 3. The extensions of the working electrode 520 may have a width between about 10 micrometers and about 50 micrometers; the extensions of the reference electrode 530 may have a width between about 100 micrometers and about 500 micrometers. The inter-electrode spacing (i.e., the distance between a given one of the working electrodes and the reference electrode extensions on either side thereof) can be between about 1 micrometer and 100 micrometers.

Figure 5C:
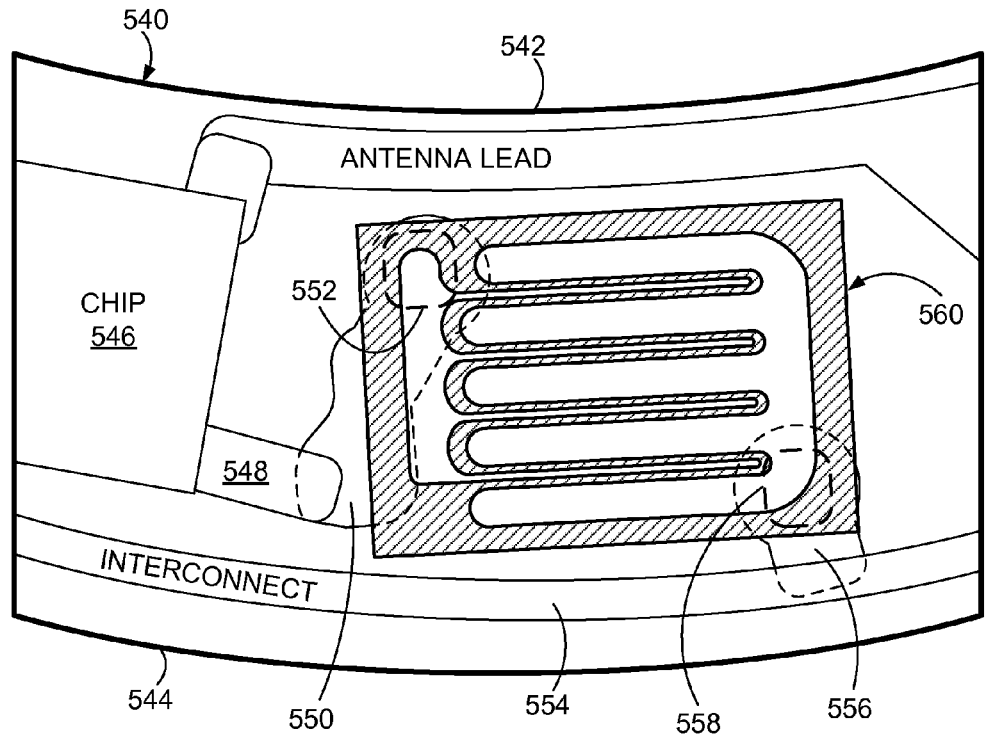
FIG. 5C shows an example electrochemical sensor chip mounted in a body-mountable device.
Figure 5D:
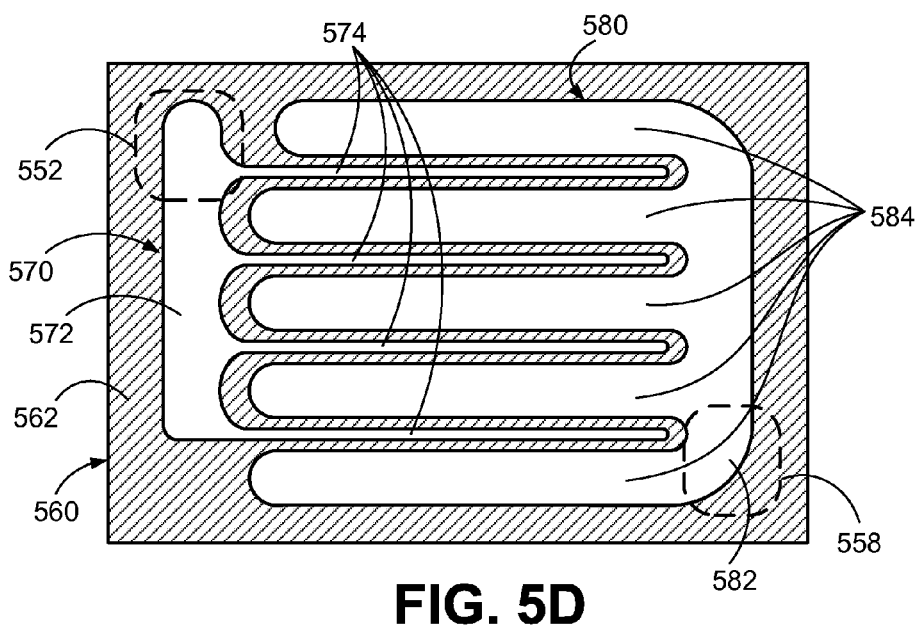
FIG. 5D is a top view of the example electrochemical sensor chip shown in FIG. 5C.

FIG. 5C shows an example electrochemical sensor chip 560 mounted in a body-mountable device. FIG. 5D is a top view of the example electrochemical sensor chip 560 shown in FIG. 5C. FIG. 5C illustrates a portion of a substrate 540 on which an electrochemical sensor chip 560 and other components are mounted. The substrate 540 is configured to be embedded in an eye-mountable device and can be similar to the substrate 230 described above in connection with FIGS. 2A-2D. The substrate 540 can be shaped as a flattened ring with an inner edge 542 and an outer edge 544. The two edges 542, 544 may both be at least approximately circular, although only a portion of each is shown in FIG. 5C.

The electrochemical sensor chip 560 includes a sensor substrate 562 on which a working electrode 570 and a reference electrode 580 are patterned in an interdigitated arrangement on a top side thereof. The sensor chip 560 also includes conductive mounting pads 552, 558 situated on the reverse side of the sensor substrate 562 (i.e., opposite the side with the electrodes 570, 580). For explanatory purposes, the approximate locations of the mounting pads 552, 558 on the reverse side of the substrate 562 is illustrated by a dashed line in FIGS. 5C and 5D. The working electrode 570 can be electrically coupled to the mounting pad 552 through a conductive via that passes through the sensor substrate 562; and the reference electrode 580 can be electrically coupled to the mounting pad 558 through a conductive via that passes through the sensor substrate 562. As shown, the working electrode 570 can overlap a portion of the mounting pad 552, and the reference electrode may overlap a portion of the mounting pad 558. Such overlapping regions may include conductive vias.

The working electrode 570 includes four extensions 574 that can each have a relatively narrow width (e.g., about 10-25 micrometers). The reference electrode 580 includes extensions 584 that extend from a base 582. As shown in FIG. 5D, the extensions 574, 584 of the two electrodes 570, 580 can be at least approximately parallel with one another. Moreover, the electrodes 570, 580 can be arranged in an interdigitated arrangement such that each of the extensions 574 of the working electrode 570 is interposed between two of the extensions 584 of the reference electrode 580 in an at least approximately symmetric manner. For instance, the inter-electrode spacing along the sidewalls of each of the working electrode extensions 574 can be symmetric along the length of the extensions. In some examples, the inter-electrode spacing can be substantially uniform, and be between about 1 micrometer and about 100 micrometers. In addition, because the electrodes 570, 580 are disposed on the sensor substrate 562, the inter-electrode spacing is relatively stable even while the substrate 540 of the body-mountable device may flex and/or deform under stress from its local environment. The sensor substrate 562 may have greater rigidity than the substrate 540 on which the antenna and chip are disposed (e.g., the sensor substrate 562 may be a silicon wafer or glass, while the substrate 540 may be parylene). In addition, because the sensor substrate 562 is only large enough to provide a mounting surface for the sensor electrodes 570, 580, and does not extend across the entire body-mountable device, the sensor substrate 562 is not subject to strains and/or deforming forces applied to the entire body-mountable device. By contrast, the substrate 540 may flex and/or deform upon the device being mounted in an eye, for example, due to differential forces across the substrate 540 as the device is mounted to a convex surface of the eye.

The controller chip 546 can be connected to the sensor chip 560 through interconnects 548, 554 that overlap (or otherwise electrically connect to) conductive terminals 550, 556 arranged to receive the mounting pads 552, 558 of the sensor chip 560. The controller chip 546 can also be connected to other components, such as an antenna, via additional interconnects and/or connection pads. For example, as shown in FIG. 5C, the chip 546 can be connected to an antenna lead, which can be formed of a patterned conductive material, such as electroplated gold, for example, that is disposed on the substrate 540 to create a loop antenna.

The electrochemical sensor chip 560 may also include a reagent layer that immobilizes a suitable reagent near the working electrode 570 so as to sensitize the electrochemical sensor to a desired analyte. In addition, the electrochemical sensor chip 560 may include one or more passivation layers, such as silicon nitride or silicon dioxide, to electrically isolate electrodes and/or conductive vias from one another and/or from the material of the substrate 562 itself.

IV. Assembly of an Example Electrochemical Sensor Chip

The electrochemical sensor chip disclosed herein may be manufactured in various ways. In example implementations, the sensor chip disclosed herein is fabricated in bulk by creating a pattern of vias through a single substrate, patterning multiple sets of sensor electrodes on the substrate with each electrode coupled to one of the vias, and then dicing the substrate to separate the individual sensor chips. Before dicing, the electrode side of the substrate may be adhered to a carrier substrate to facilitate fabrication of the conductive pads on the reverse side. Conductive pads can be patterned on the reverse side with each conductive pad coupled to one of the vias (and one of the sensor electrodes). Once formed, the individual sensor chips can then be flip-chip mounted into a body-mountable or implantable device. An example manufacturing process is described below in connection with FIGS. 6A-6K.

FIGS. 6A, 6B, 6C, 6D, 6E, 6F, 6G, 6H, 6I, 6J, and 6K illustrate stages of fabricating an electrochemical sensor chip, according to an example embodiment. To facilitate understanding, a region of a substrate that includes only a single sensor chip is illustrated. In practice, however, a manufacturing process may involve fabricating many sensor chips simultaneously on a single substrate that is then diced to separate the individual sensor chips. For instance, a 12 inch wafer may be used to fabricate over 100,000 sensor chips.

Figure 6A:
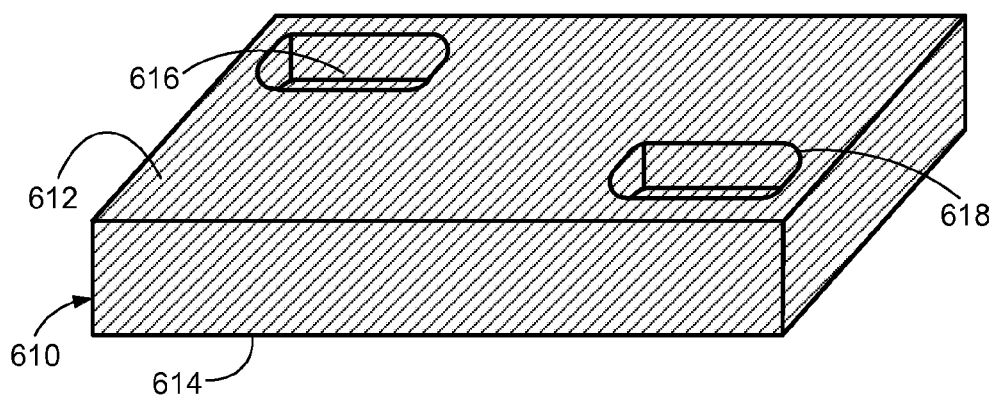
FIGS. 6A, 6B, 6C, 6D, 6E, 6F, 6G, 6H, 6I, 6J, and 6K illustrate stages of fabricating an electrochemical sensor chip, according to an example embodiment.

FIG. 6A is an aspect view of a substrate 610 having a top side 612 and a reverse side 614 opposite the top side 612. The substrate 610 can be a silicon wafer, for example. Depressions 616, 618 have been formed in the top side 612 of the substrate 610. The depressions 616, 618 are positioned at locations on the substrate 610 for vias through the substrate 610. The depressions 616, 618 may be formed, for example, by laser ablation of the substrate 610 or by etching the substrate 610. In one approach, the depressions 616, 618 may be formed using deep reactive ion etching. The depressions 616, 618 may or may not fully penetrate the substrate 610 (i.e., the depressions 616, 618 may or may not reach the reverse side 614).

As shown in FIG. 6A, the depressions 616, 618 have a depth that is less than the thickness of the substrate 610. In this example, the substrate 610 may be thinned from the reverse side 614 (e.g., by polishing). The thinning is sufficient to expose the depressions 616, 618 from the reverse side 614. Thus, after thinning, the depressions 616, 618 penetrate through the thinned substrate 610 from side 612 to reverse side 614.

Figure 6B:
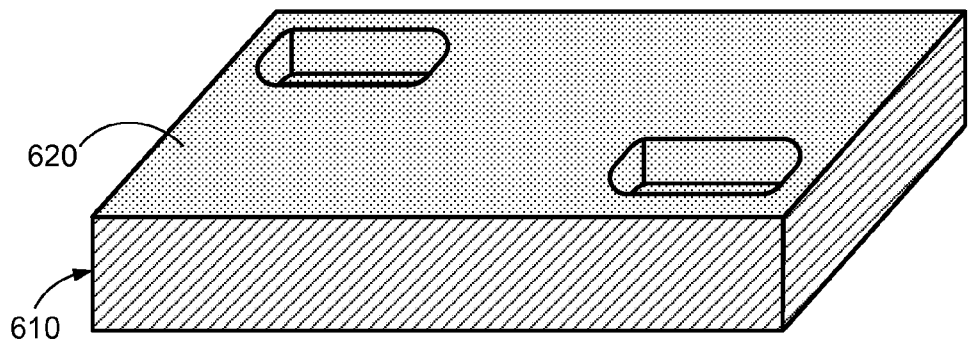

FIG. 6B is an aspect view of the sensor substrate 610 after being coated with a passivation layer 620. The passivation layer 620 can be silicon dioxide or silicon nitride, or another electrically insulating material. The passivation layer 620 may be sputtered over the top side 612 of the substrate 610 such that the side walls of the depressions are coated with the passivation material 620. The passivation layer 620 electrically insulates the substrate 610 from conductive material that will be formed thereon. For instance, the substrate 610 may be a silicon wafer or another semi-conductive material and the passivation layer 620 coating the substrate 610 can help prevent conductive paths from being created through the substrate 610 when voltage is applied.

Figure 6C:
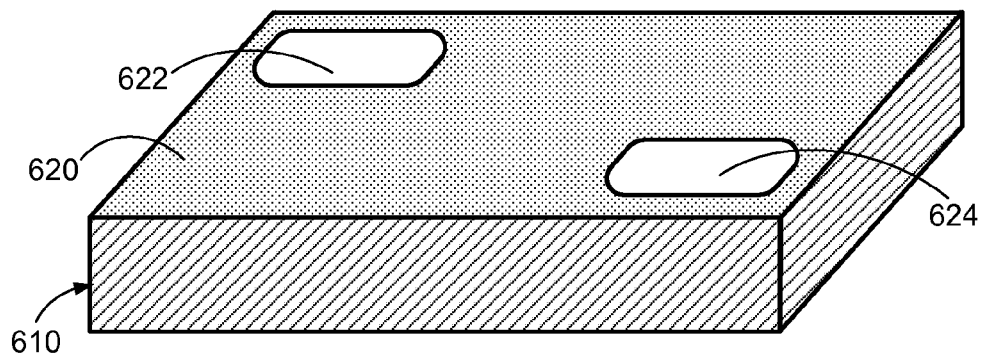

FIG. 6C is an aspect view of the sensor substrate 610 after the depressions 616, 618 have been filled with conductive material 622, 624. The conductive material 622, 624 occupying the depressions 616, 618 creates conductive vias through the substrate 610. The conductive material 622, 624 may include gold or another conductive material that is electroplated over a seed layer patterned on sidewalls of the depressions 616, 618. The seed layer may be a conductive material different from the material that is electroplated. Thus, the electroplated conductive material 622, 624 may be disposed along the sidewalls of the depression 616, 618 and may or may not fully occupy the depressions.

Figure 6D:
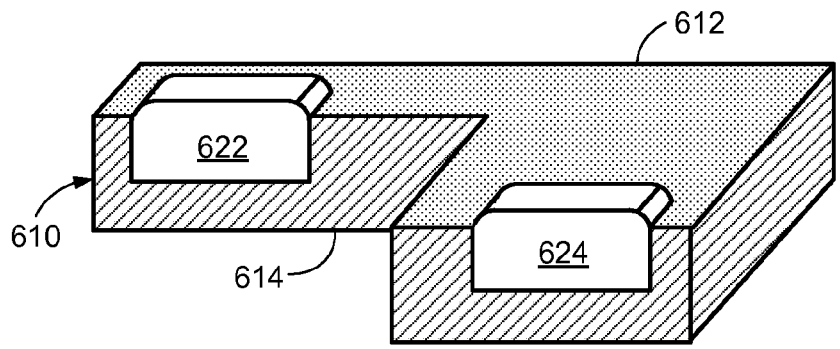

FIG. 6D is a side cut-away view of the substrate 610 which shows the conductive material 622, 624 extending beyond the plane of the top surface 612 of the substrate 610.

Figure 6E:
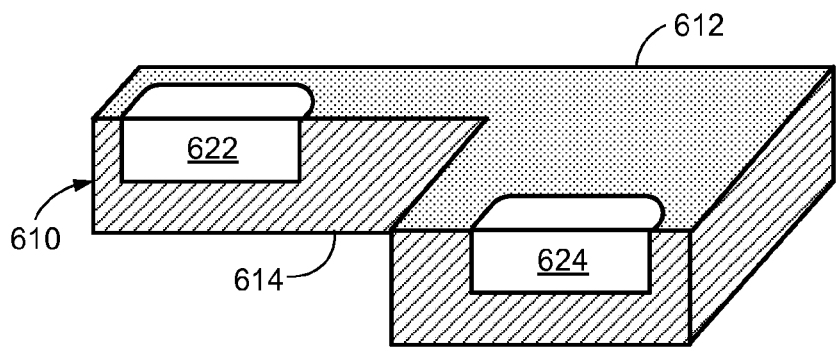

After filling the depressions 616, 618 with the conductive material, some of the conductive material 622, 624 may protrude out of the depressions 616, 618, beyond the plane of the top surface 612. FIG. 6E shows a side cut-away view of the substrate 610 after the top surface 612 has been polished to remove the protruding conductive material 622, 624 shown in FIG. 6D. After polishing, the remaining conductive material within the depressions is substantially coplanar with the top surface 612 of the substrate 610.

Figure 6F:
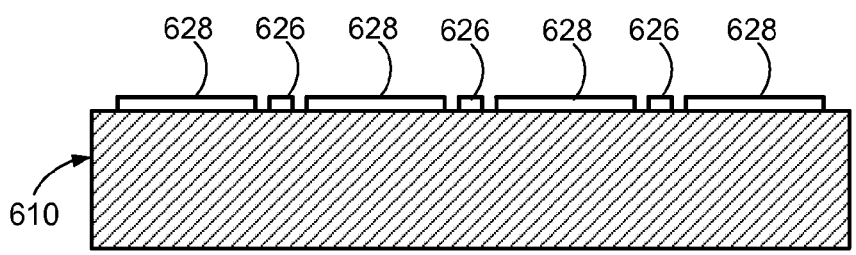

FIG. 6F is a cross-sectional view of the substrate 610 after patterning a working electrode 626 and reference electrode 628 on the top surface. The cross-sectional view shows a view that traverses interdigitated extensions of the two electrodes 626, 628. The working electrode 626 includes three extensions, and each of the working electrode extensions can be situated between two extensions of the working electrode 628. The working electrode 626 and reference electrode 628 may be patterned in an interdigitated arrangement similar to the electrode arrangement described above in connection with FIGS. 5A-5D. Note that the illustration of the patterned electrodes 626, 628 is provided for explanatory purposes and is not necessarily drawn to scale. In particular, the thickness of the electrodes 626, 628 may be less than one micrometer, while the thickness of the substrate 610 may be about 500 micrometers, but the electrodes are illustrated so as to show the relative spacing of the patterned electrodes. The electrodes 626, 628 are patterned such that each overlaps one of the polished surfaces of the conductive material 622, 624. For instance, the working electrode 626 can be patterned to overlap the conductive material 622, and thereby be electrically coupled to the conductive material 622; and the reference electrode 628 can be patterned to overlap the conductive material 624, and thereby be electrically coupled to the conductive material 624.

Figure 6G:
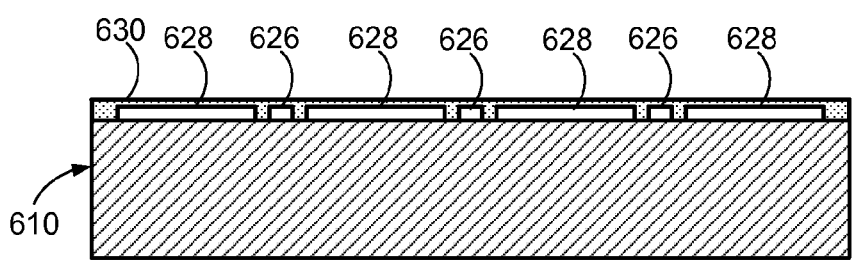

FIG. 6G is a cross-sectional view of the substrate 610 with electrodes 626, 628 patterned thereon after a passivation layer 630 has been formed over the electrodes 626, 628. The passivation layer 630 may include silicon nitride or silicon dioxide or another electrically insulating material.

Figure 6H:
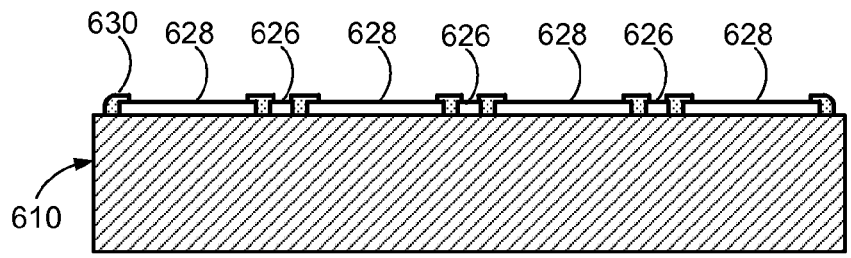

FIG. 6H is a cross-sectional view of the substrate 610 after the passivation layer 630 has been selectively removed to expose the electrodes 626, 628. The electrodes 626, 628 may be exposed by ablating and/or etching the passivation layer 630 in a pattern (e.g., using resists patterned with photolithography, masking or another technique). The excised regions of the passivation layer 630 thus define the exposed surface area of the two electrodes 626, 628. The exposed surface area of the sensor electrodes 626, 628 define the active area of the electrodes 626, 628 (i.e., the region of the working electrode 626 that electrochemically reacts with a sample fluid. The patterned passivation material 630 can also define the inter-electrode spacing between the electrodes 626, 628. In some examples, the patterned passivation layer 630 can be used to provide a sensor electrode with an exposed surface area that is less than the area of conductive material disposed on the substrate 610. As a result, the conductive material disposed on the substrate 610 to form the electrode 626 may have a surface area suitable for adhering to the substrate 610. However, the exposed surface area of the electrode 626, which defines the electrochemical reaction rate of the sensor when exposed to a fluid, and thus the sensitivity of the sensor, may be less than the area adhered to the substrate 610. For instance, a working electrode may be patterned with a width of about 25 micrometers, but the patterned passivation layer can expose a width of the working electrode that is about 10 micrometers. In some cases, a working electrode may be formed with an exposed width less than 1 micrometer. As such, the conductive material formed on the substrate to define the electrodes 626, 628 can be patterned in an arrangement that provides a desired level of adhesion with the substrate, but the amount of surface area of the electrodes to expose (and thus the sensitivity of the sensor) can be selected independent of the ability of the conductive material to adhere to the substrate 610.

In another example, rather than patterning the passivation layer 630 and then selectively etching or otherwise removing the passivation layer to expose the electrodes 626, 628, passivation material may be patterned to occupy selected regions as shown in FIG. 6H. In yet another example, the passivation layer may be omitted entirely.

Figure 6I:
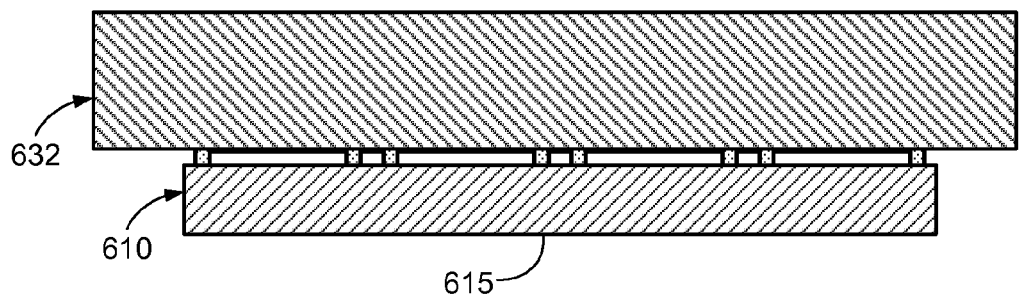

FIG. 6I is a cross-sectional view showing the substrate 610 adhered to a carrier substrate 632. The carrier substrate 632 is removably adhered to the electrode 626, 628 on the top side 612 of the substrate 610, which allows the reverse side 614 of the substrate 610 to be manufactured. The reverse side of the substrate 610 is then polished to thin the substrate 610, which results in the polished surface 615. The polishing process can thin the substrate 610 to expose the conductive material 622, 624 filling the depressions 616, 618. The depths of the earlier-formed depressions 616, 618 can be selected to be at least as great as the thickness of the substrate 610 following thinning. Thus, following the polishing process, the conductive material passes through the entire remaining thickness of the substrate and thereby provides a conductive path through the substrate 610. Following thinning, the thickness of the substrate 610 may be between about 50 micrometers and about 100 micrometers, whereas the initial substrate may have a thickness of about 500 micrometers. Although the final thickness of the substrate 610 may be selected based on a variety of factors including the structural integrity of the thinned substrate material, and the size/weight limitations of application(s) in which the sensor chip will be incorporated.

Figure 6J:
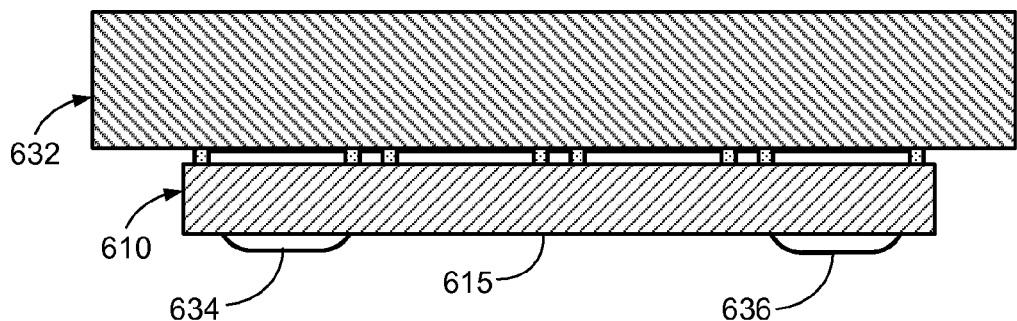

FIG. 6J shows a side view after forming conductive mounting pads 634, 636 over the polished surface 615 while the substrate 610 is adhered to the carrier substrate 632. For instance, the mounting pad 634 can be formed by patterning conductive material to overlap the exposed depression 616 and conductive material 622 therein, and thereby electrically couple the mounting pad 634 to the working electrode 626 through the conductive material 622. Similarly, the mounting pad 636 can be formed by patterning conductive material to overlap the exposed depression 618 and conductive material 624 therein, and thereby electrically couple the mounting pad 636 to the reference electrode 628 through the conductive material 624. The conductive mounting pads 634, 636 can be formed by patterning a conductive seed layer over the polished surface in a pattern that overlaps the conductive material 622, 624 in the exposed depressions, and then electroplating gold or another material to a desired thickness. In some examples, the mounting pads 634, 636 may extend about 10 micrometers beyond the plane of the polished surface 615. The mounting pads 634, 636 can be patterned generally in any arrangement on the polished surface 615 so as to correspond to conductive terminals on which the completed sensor chip will be flip-chip mounted. For example, each mounting pad 634, 636 may occupy approximately half of the polished surface, which may help provide additional tolerance when placing the completed sensor chip over corresponding terminals. Other examples are possible.

Figure 6K:
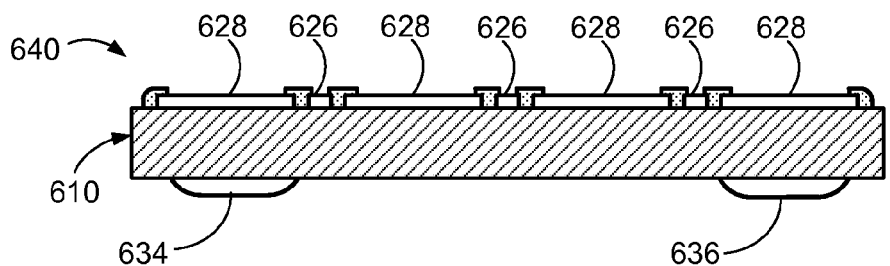

FIG. 6K shows a side cross-sectional view of the completed sensor chip 640 after being released from the carrier substrate 632. Releasing the sensor chip 640 may involve rinsing the substrate 610 with a solvent to release an adhesive bond between the carrier substrate 632 and the electrodes 626, 628 and/or the sensor substrate itself. Following release, the sensor chip 640 includes a working electrode 626 and a reference electrode 628 patterned on one side of the sensor substrate 610, and each of the electrodes 626, 628 is electrically coupled to one of the mounting pads 634, 636 patterned on the reverse side of the sensor substrate 610.

As noted above, the manufacturing process described in connection with FIGS. 6A-6K may be performed so as to form multiple sensor chips on a common substrate. The substrate can be diced to separate the individual sensor chips.

Once completed, the sensor chip 640 may be incorporated in a body-mountable device. For example, the sensor chip 640 could be incorporated in an eye-mountable device similar to the eye-mountable device 210 described above by flip-chip mounting the conductive mounting pads 634, 636 to corresponding terminals on a substrate embedded in such a device (e.g., similar to the description of the sensor chip 560 in FIGS. 5C-5D). A controller can be electrically coupled to the sensor chip 640 through interconnects and can the operate the sensor chip 640 by applying a voltage to the electrodes 626, 628, measuring a current through the working electrode 626, and using an antenna to wirelessly indicate the current measurement.

Figure 7:
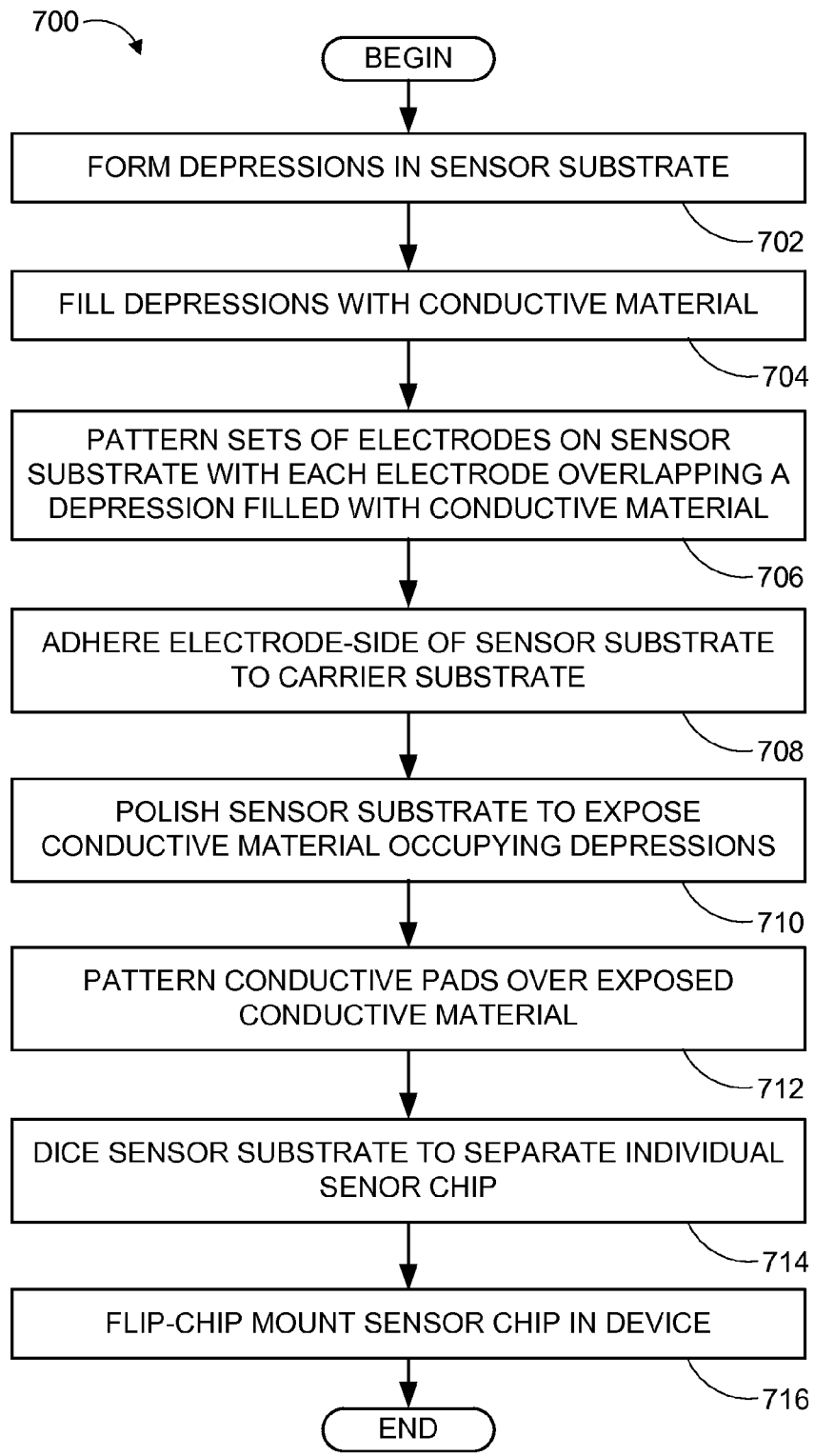
FIG. 7 is a flowchart of an example process for fabricating an electrochemical sensor chip.

FIG. 7 is a flowchart of an example process 700 for producing an electrochemical sensor chip. At block 702, depressions are formed in a sensor substrate. For example, a combination of selectively etchable materials and/or photoresists can be patterned to selectively expose areas at which to form depressions, and deep reactive ion etching can be used to etch depressions into a silicon wafer. In another example, depressions can be formed using a laser system to oblate material from the substrate to a desired depth. At block 704, the depressions can be filled with a conductive material. For example, a seed layer can be sputtered or otherwise patterned on the sidewalls of the depressions and a conductive material can be electroplated over the seed layer. Each depression filled by conductive material will provide an electrical connection through the substrate in the completed sensor chips. In some examples, the top surface of the substrate can be polished to remove any conductive material that extends beyond the plane of the substrate. At block 706, sets of electrodes can be patterned over the top surface. Each electrode can overlap one of the conductive-material-filled depressions, such that each electrode is electrically coupled to one of the electrical pathways into the substrate provided by the conductive material filled depressions. At block 708, the electrode-side of the sensor substrate can be adhered to a carrier substrate, which facilitates processing of the reverse side of the substrate. At block 710, the sensor substrate can be polished from the reverse side to thin the substrate at least until the conductive material occupying the depressions becomes exposed. Following thinning of the substrate, the conductive material in each depression passes through the entire remaining thickness of the substrate and thereby provides a set of electrical pathways through the substrate, with each pathway electrically coupled to one of the electrodes. At block 712, conductive pads can be patterned over the polished surface of the substrate. Each conductive pad can be patterned to overlap one of the conductive-material-filled depressions, such that each electrode is electrically coupled to one of the electrical pathways into the substrate provided by the conductive material filled depressions, and also to one of the electrodes. At block 714, the substrate can be released from the carrier substrate and diced, which separates the individual sensor chips from one another. At block 716, the sensor chip can be mounted to a substrate for a body-mountable device or an implantable device where it can be used to measure analyte concentrations. For example, the sensor chip can be flip-chip mounted to conductive terminals on a substrate that also includes a controller and antenna, similar to the eye-mountable and/or body-mountable sensor platforms described in connection with FIGS. 1-2, for example. The substrate for the body-mountable device may be encapsulated, partially or entirely, by polymeric material configured to mount to a body surface or be implanted within a host.

V. Additional Embodiments

It is particularly noted that while the various electronics platforms are described herein by way of example as an eye-mountable device or an ophthalmic device, it is noted that the disclosed systems and techniques for configurations of electrochemical sensor chips can be applied in other contexts as well. For example, contexts in which analyte concentration is measured in-vivo and/or from relatively small sample volumes, or are constrained to small form factors (e.g., implantable bio-sensors or other electronics platforms) may employ the systems and processes described herein. In one example, an implantable medical device that includes an electrochemical sensor chip encapsulated in biocompatible material and implanted within a host. The implantable medical device may include a circuit configured to output an indication of an analyte concentration measurement (e.g., an amperometric current reading). Reading and/or control devices can communicate with the implantable medical device to obtain measurements.

For example, in some embodiments, the electronics platform may include a body-mountable device, such as a tooth-mountable device. In some embodiments, the tooth-mountable device may take the form of or be similar in form to the body-mountable device 110 and/or the eye-mountable device 210. For instance, the tooth-mountable device may include a biocompatible polymeric material or a transparent polymer that is the same or similar to any of the polymeric materials or transparent polymers described herein and a substrate or a structure that is the same or similar to any of the substrates or structures described herein, although the exterior surface of the polymeric material may be formed to facilitate tooth-mounting, rather than eye-mounting. In such an arrangement, the tooth-mountable device may be configured to measure analyte concentration of a fluid (e.g., saliva) of a user wearing the tooth-mountable device. Other body mounting locations are also possible.

Moreover, in some embodiments, a body-mountable device may comprise a skin-mountable device. In some embodiments, the skin-mountable device may take the form of or be similar in form to the body-mountable device 110 and/or the eye-mountable device 210. For instance, the skin-mountable device may include a biocompatible polymeric material or a transparent polymer that is the same or similar to any of the polymeric materials or transparent polymers described herein and a substrate or a structure that is the same or similar to any of the substrates or structures described herein, although the exterior surface of the polymeric material may be formed to facilitate skin-mounting, rather than eye-mounting. In such an arrangement, the body-mountable device may be configured to measure analyte concentration of a fluid (e.g., perspiration, blood, etc.) of a user wearing the body-mountable device.

In example embodiments, the example system can include one or more processors, one or more forms of memory, one or more input devices/interfaces, one or more output devices/interfaces, and machine-readable instructions that when executed by the one or more processors cause the system to carry out the various functions, tasks, capabilities, etc., described above.

As noted above, in some embodiments, the disclosed techniques can be implemented by computer program instructions encoded on a non-transitory computer-readable storage media in a machine-readable format, or on other non-transitory media or articles of manufacture. Such computing systems (and non-transitory computer-readable program instructions) can be configured according to at least some embodiments presented herein, including the processes shown and described in connection with FIGS. 4A-4B and 7.

The programming instructions can be, for example, computer executable and/or logic implemented instructions. In some examples, a computing device is configured to provide various operations, functions, or actions in response to the programming instructions conveyed to the computing device by one or more of the computer readable medium, the computer recordable medium, and/or the communications medium. The non-transitory computer readable medium can also be distributed among multiple data storage elements, which could be remotely located from each other. The computing device that executes some or all of the stored instructions can be a microfabrication controller, or another computing platform. Alternatively, the computing device that executes some or all of the stored instructions could be remotely located computer system, such as a server.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:

1. A device comprising:
 a polymeric material, wherein the polymeric material has a shape that includes a mounting surface formed to be mounted to an external body surface;
 a first substrate at least partially embedded within the polymeric material;
 a conductive interconnect disposed on the first substrate;
 an electrochemical sensor disposed on the first substrate, wherein the electrochemical sensor comprises:
 a sensor substrate different from the first substrate, wherein the sensor substrate includes a first side and a second side opposite the first side;
 a working electrode disposed on the first side of the sensor substrate;
 a reference electrode disposed on the first side of the sensor substrate;
 a first conductive connection pad disposed on the second side of the sensor substrate, wherein the first conductive connection pad is electrically coupled to the working electrode; and
 a second conductive connection pad disposed on the second side of the sensor substrate, wherein the second conductive connection pad is electrically coupled to the reference electrode; and
 a controller electrically connected to the electrochemical sensor via the first and second conductive connection pads, wherein the controller is electrically connected to the first conductive connection pad via the interconnect, wherein the controller is disposed on the first substrate, and wherein the controller is configured to: apply a voltage between the working electrode and the reference electrode sufficient to generate an amperometric current related to the concentration of an analyte in a fluid to which the device is exposed.

2. The device of claim 1,
 wherein an electrical path that couples the working electrode and the first conductive connection pad includes a first via, wherein the first via comprises conductive material that at least partially occupies a first aperture through the sensor substrate, and
 wherein an electrical path that couples the reference electrode and the second conductive connection includes a second via, wherein the second via comprises conductive material that at least partially occupies a second aperture through the sensor substrate.

3. The device of claim 1, wherein the sensor substrate includes a semiconductor, and wherein the electrochemical sensor further comprises a passivation layer disposed on the first side of the sensor substrate interposed between at least a portion of the working electrode and at least a portion of the reference electrode.

4. The device of claim 3, wherein the sensor substrate includes silicon, and wherein the passivation layer includes silicon dioxide.

5. The device of claim 1, wherein the reference electrode and the working electrode each include multiple extensions arranged on the sensor substrate so as to be interdigitated with one another.

6. The device of claim 4, wherein each of the multiple extensions of the working electrode include first and second sides that are both adjacent to, and substantially equidistant from, respective ones of the multiple extensions of the reference electrode.

7. The device of claim 1, wherein the first substrate includes at least one of: parylene, polyamine, or polyethylene terephthalate.

8. The device of claim 1, wherein the controller is electrically coupled to the electrochemical sensor via an electrical path that includes a first terminal and a second terminal each disposed on the first substrate, wherein the first terminal is electrically connected to the first conductive connection pad, and wherein the second terminal is electrically connected to the second conductive connection pad.

9. The device of claim 1, wherein the polymeric material includes a channel situated such that the fluid is conveyed through the channel to the electrodes of the electrochemical sensor.

10. The device of claim 1, wherein the working electrode is partially coated with a passivation layer such that a surface area of the working electrode that is exposed to the fluid is less than a surface area of the working electrode that is adhered to the sensor substrate.

11. The device of claim 1, wherein the polymeric material has a concave surface and a convex surface, wherein the concave surface is configured to be removably mounted over a corneal surface and the convex surface is configured to be compatible with eyelid motion when the concave surface is so mounted.

12. A method comprising:
 applying, via controller, a voltage between a working electrode and a reference electrode of an electrochemical sensor, wherein the applied voltage is sufficient to generate an amperometric current related to the concentration of an analyte in a fluid to which the electrochemical sensor is exposed, wherein the working electrode and the reference electrode are each disposed on a first side of a sensor substrate, wherein a first conductive pad and a second conductive pad are situated on a second side of the sensor substrate opposite the first side, the first conductive pad and the second conductive pad being electrically coupled to the working electrode and the reference electrode, respectively, wherein the controller, a conductive interconnect, and the electrochemical sensor are disposed on a first substrate different from the sensor substrate, wherein the controller is electrically coupled to the working electrode and the reference electrode via the first and the second conductive pads, respectively, wherein the controller is electrically connected to the first conductive connection pad via the interconnect, and wherein the first substrate is at least partially embedded in a polymeric material, wherein the polymeric material has a shape that includes a mounting surface formed to be mounted to an external body surface; and measuring the amperometric current using the controller.

\* \* \* \* \*